US006711941B2

(12) United States Patent
Braithwaite et al.

(10) Patent No.: US 6,711,941 B2
(45) Date of Patent: Mar. 30, 2004

(54) APPARATUS AND METHODS FOR MEASURING EXTENSIONAL RHEOLOGICAL PROPERTIES OF A MATERIAL

(75) Inventors: Gavin J. C. Braithwaite, Cambridge, MA (US); Stephen H. Spiegelberg, Winchester, MA (US); Gareth H. McKinley, Acton, MA (US)

(73) Assignee: Cambridge Polymer Group, Inc., Boston, MA (US)

( * ) Notice: Subject to any disclaimer, the term of this patent is extended or adjusted under 35 U.S.C. 154(b) by 62 days.

(21) Appl. No.: 09/928,643

(22) Filed: Aug. 13, 2001

(65) Prior Publication Data

US 2002/0116987 A1 Aug. 29, 2002

Related U.S. Application Data

(60) Provisional application No. 60/224,786, filed on Aug. 14, 2000.

(51) Int. Cl.[7] .............................................. G01N 11/00
(52) U.S. Cl. ..................... 73/54.01; 73/54.13; 73/53.01
(58) Field of Search ............................ 73/54.01, 54.13, 73/53.01

(56) References Cited

U.S. PATENT DOCUMENTS

| 3,569,722 | A | * | 3/1971 | Denson ..................... 250/218 |
| 3,640,127 | A | | 2/1972 | Meissner .................... 73/95.5 |
| 3,693,425 | A | | 9/1972 | Starita et al. ................. 73/133 |
| 3,832,886 | A | * | 9/1974 | Pliskin ...................... 73/54.13 |
| 4,466,274 | A | * | 8/1984 | Starr, Jr. .................... 73/54.01 |
| H93 | H | | 7/1986 | Matta et al. ................... 73/56 |
| 5,040,410 | A | * | 8/1991 | Chu et al. .................... 73/54.01 |
| H976 | H | * | 11/1991 | Matta et al. ................... 73/54.01 |
| 5,269,174 | A | * | 12/1993 | Chiba ........................ 73/54.01 |
| 5,279,149 | A | * | 1/1994 | Williams et al. ............. 73/54.01 |
| 5,357,784 | A | | 10/1994 | Collier ...................... 73/54.14 |
| 5,456,105 | A | * | 10/1995 | James ....................... 73/54.01 |
| 5,457,987 | A | * | 10/1995 | Bulou et al. ................. 73/64.49 |
| 5,559,284 | A | | 9/1996 | Matta et al. ................. 73/64.52 |
| 5,590,560 | A | * | 1/1997 | Joos et al. ................... 73/64.48 |
| 5,686,659 | A | * | 11/1997 | Neel et al. ................... 73/53.01 |
| 5,744,703 | A | * | 4/1998 | Krenceski et al. ........... 73/54.01 |
| 5,789,664 | A | * | 8/1998 | Neel et al. ................... 73/53.01 |
| 5,792,944 | A | * | 8/1998 | Lennert et al. .............. 73/64.43 |
| 5,886,252 | A | * | 3/1999 | Lennert et al. .............. 73/53.01 |
| 5,900,539 | A | | 5/1999 | Tremblay et al. ........... 73/54.13 |
| 6,189,370 | B1 | * | 2/2001 | Neel et al. ................... 73/53.01 |
| 6,386,016 | B1 | * | 5/2002 | Gleissle ..................... 73/54.01 |
| 6,575,017 | B1 | * | 6/2003 | Neel et al. ................... 73/53.01 |

FOREIGN PATENT DOCUMENTS

| EP | 0 014 025 | 7/1980 |
| EP | 0 394 184 | 10/1990 |
| FR | 2 756 924 | 12/1996 |
| GB | 1 476 935 | 6/1997 |
| WO | 00/28321 | 5/2000 |

OTHER PUBLICATIONS

Meissner, J. & Hostettler J., "A new elongational rheometer for polymer melts and other highly viscoelastic liquids," Rheol Acta 33:1–21 (1994).

(List continued on next page.)

Primary Examiner—Hezron Williams
Assistant Examiner—Rodney T Frank
(74) Attorney, Agent, or Firm—Bowditch & Dewey, LLP

(57) ABSTRACT

Apparatus and methods for evaluating the rheological properties of Newtonian and non-Newtonian liquids and melts employs the principle of capillary breakup following rapid stretching of the fluid between two plates. The apparatus includes opposed surfaces defining a sample site disposed therebetween. A liquid sample undergoes an extensional deformation between the opposed surfaces which separate using a user-defined motion profile. The time profile of the diameter of the liquid filament is monitored and recorded as a function of time. Preferred embodiments of the present invention include data analysis of the diameter of the filament as a function of time which provides information regarding rheological parameters including, but not limited to, extensional viscosity versus strain.

46 Claims, 15 Drawing Sheets

OTHER PUBLICATIONS

Gaudet, S., et al, "Extensional deformation of Newtonian liquid bridges," Phys. Fluids 8, 2568–2579 (Oct. 1996).

Eggers, J., "Nonlinear dynamics and breakup of free–surface flows," Review of Modern Physics, 69, 865–929 (Jul 1997).

Liang, R. F. & Mackley M. R., "Rheological characterization of the time and strain dependence for polyisobutylene solutions," Journal of Non–Newtonian Fluid Mech, 52, 387–405 (1994).

Papageorgiou, D. T., "On the breakup of viscous liquid thread," Phys. Fluids 7, 1529–1544 (Jul. 1995).

Bousfield, D.W. et al., "Nonlinear Analysis of the Surface Tension Driven Breakup of Viscoelastic Filaments," Journal of Non–Newtonian Fluid Mechanics, 21, 79–97, (1986).

Renardy, M., "A numerical study of the asymptotic evolution and breakup of Newtonian and viscoelastic jets," Journal of Non–Newtonian Fluid Mechanics, 59, 267–282, (1995).

Anna, S. L., "Elasto–capillary thinning and breakup of model elastic liquids," Journal of Rheology, 45(1), 115–138 (2001).

Entov, V. M. et al., "Rapid stretching of polymer solutions," Sov. Phys, Dokl., 33(8), 628–630, (1988).

Barnes, H. A. et al., "An Introduction to Rheology," Elsevier, 75–80 (1989).

Bazilevsky et al. (1990) "Liquid Filament Microrheometer and Some of its Applications," *Third European Rheology Conference and Golden Jubilee Meeting of the British Society of Rheology, Ed. D.R. Oliver*, pp. 41–43.

Bazilevskii et al. (1997) "Failure of Polymer Solution Filaments," *Polymer Science, Series A* 39:316–324.

Berg et al. (1994) "Measurement of Extensional Viscosity by Stretching Large Liquid Bridges in Microgravity," *J. Non–Newtonian Fluid Mech.* 55:307–319.

Eggers (1993) "Universal Pinching of 3D Axisymmetric Free–Surface Flow," *Phys. Rev.* 71:3458–3460.

Entov et al. (1984) "Influence of Elastic Stresses on the Capillary Breakup of Jets of Dilute Polymer Solutions," Translated from Izvestiya Akademii Nauk SSSR Mekhanika Zhidkosti i Gaza 1:27–35 Plenum Publishing Corporation.

Entov et al. (1997) "Effect of a Spectrum of Relaxation Times on the Capillary Thinning of A Filament of Elastic Liquid," *J. Non–Newtonian Fluid Mech.* 72:31–53.

James et al. (1993) "A Critical Appraisal of Available Methods for the Measurement of Extensional Properties of Mobile Systems," *Techniques in Rheological Measurement*, Ed. A.A. Collyer, pp. 33–53.

Jones et al. (1982) "The Stringiness of Dilute Polymer Solutions," *Journal of Non–Newtonian Fluid Mechanics* 11:257–268.

Keiller (1992) "Extending Filaments of An Oldroyd Fluid," *Journal of Non–Newtonian Fluid Mechanics* 42:37–48.

Kolte et al. (1999) "Capillary Thinning of Polymeric Filaments," *J. Rheol.* 43:609–625.

Matta et al. (1990) "Liquid Stretching Using a Falling Cylinder," *Journal of Non–Newtonian Fluid Mechanics* 35:215–229.

McKinley et al. (2000) "How to Extract the Newtonian Viscosity from Capillary Breakup Measurements in a Filament Rheometer," *J. Rheol.* 44:653–670.

Munstedt et al. (1981) "Elongational Properties And Molecular Structure of Polyethylene Melts," *Rheol. Acta* 20:211–221.

Slobozhanin et al. (1993) "Stability of Liquid Bridges Between Equal Disks in An Axial Gravity Fluid," *Phys. Fluids A* 5:1305–1314.

Spiegelberg et al. (1996) "The Role of End–effects on Measurements of Extensional Viscosity in Filament Stretching Rheometers," *J. Non–Newtonian Fluid Mech.* 64:229–267.

Stelter et al. (2000) "Validation and Application of A Novel Elongational Device for Polymer Solutions," *J. Rheol.* 44:595–616.

Stelter et al. (1999) "Shear and Extensional Investigations in Solutions of Grafted/Ungrafted Amylopectin and Polyacrylamide," *Journal of Applied Polymer Science* 74:2773–2782.

Szabo (1997) "Transient Filament Stretching Rheometer I: Force Balance Analysis," *Rheol. Acta* 36:277–284.

Tirtaatmadja et al. (1993) "A Filament Stretching Device for Measurement of Extensional Viscosity," *J. Rheol.* 37:1081–1102.

Tripathi et al. (2000) "Studying the Extensional Flow and Breakup of Complex Fluids Using Filament Rheometers," *Proceedings of the International Congress of Rheology* 3:55–57.

Tripathi et al. (2000) "Using Filament Stretching Rheometry to Predict Strand Formation and Processability in Adhesives and Other Non–Newtonian Fluids," *Rheol Acta* 39:321–337.

Vinogradov et al. (1970) "Extension of Elastic Liquids: Polyisobutylene," *Journal of Polymer Science* 8:1–17.

Wunderlich et al. (1999) "Shear and Extensional Rheological Investigations in Solutions of Grafted and Ungrafted Polysaccharides," *J. Applied Polymer Science* 77:3200–3209.

"The CaBER System" (Apr., 2000) Cambridge Polymer Group product brochure shown at Society for Biomaterials Trade Show, Hawaii (Apr., 2000), and available on the company's web site beginning in Apr., 2000, pp. 1–2.

* cited by examiner

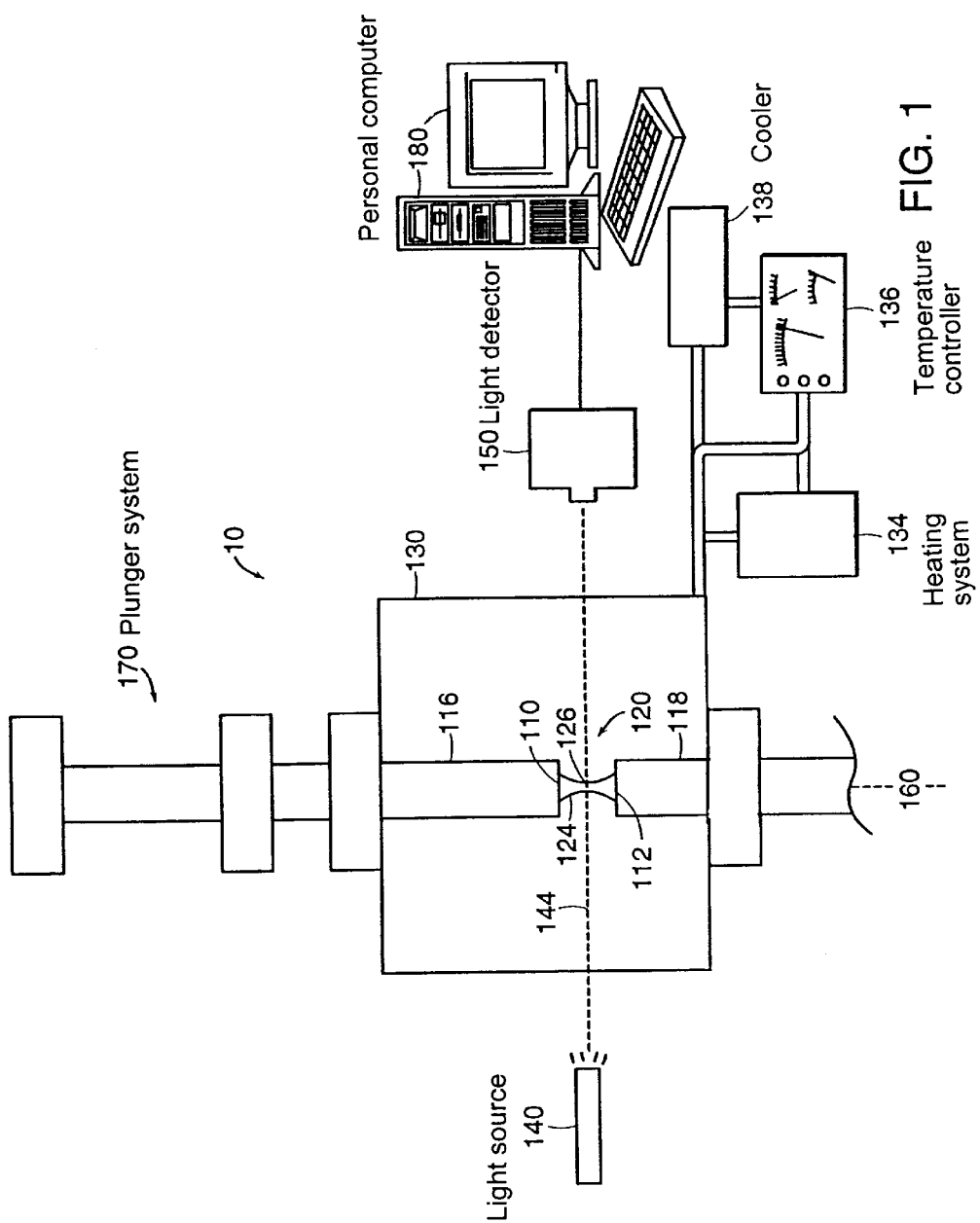

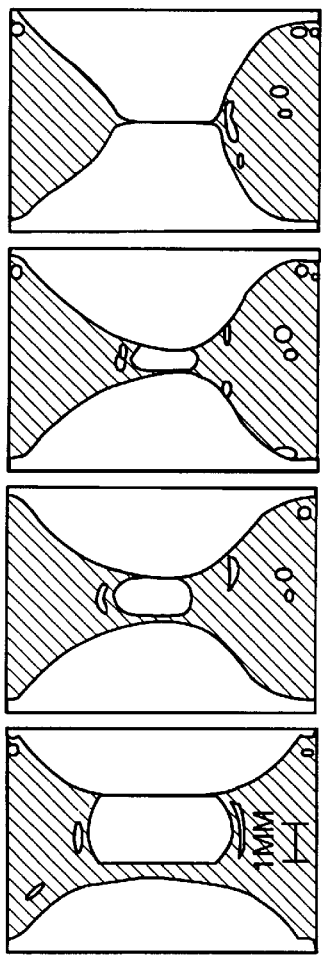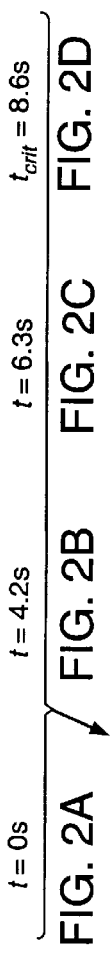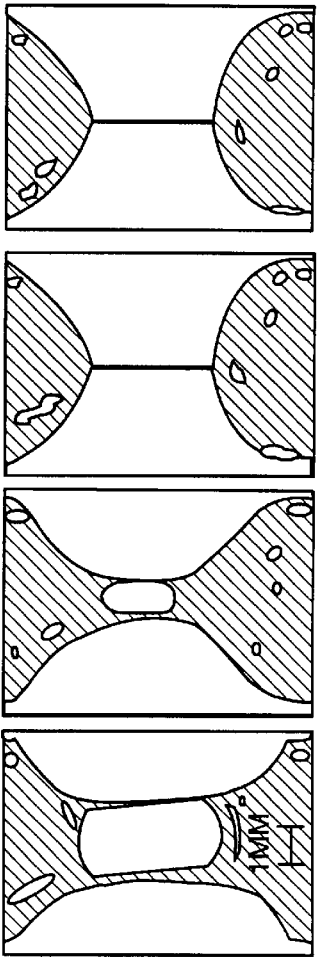

APPARATUS AND METHODS FOR MEASURING EXTENSIONAL RHEOLOGICAL PROPERTIES OF A MATERIAL

RELATED APPLICATION

This application claims the benefit of the filing date of U.S. Provisional Patent Application Ser. No. 60/224,786, filed on Aug. 14, 2000, entitled "A Device And Method For Measuring Extensional Rheological Properties Of Materials" by Braithwaite et al., which is incorporated by reference in its entirety herein.

TECHNICAL FIELD

This invention relates to an apparatus and method for measuring rheological properties of a material. Particularly, this invention relates to measuring Theological properties of a material including viscosity, surface tension, elasticity, relaxation time, association time, and yield stress for liquids, solutions, suspensions, and melts.

BACKGROUND INFORMATION

Extensional flows are common in most industrial processes but are often poorly understood. Fluids are infrequently well-characterized in their extension. The concept of extensional rheometry is analogous to that of torsional shear rheometry. In a shear test, a small quantity of fluid is sandwiched between two plates. One plate is either rotated at a constant rate, or oscillated at a fixed frequency. By measuring the torque required to maintain the rotation rate, or the delay in the applied torque compared to the forced oscillation, one can compute a shear viscosity as a function of shear rate or oscillation frequency.

Instead of obtaining the shear viscosity and other related parameters by applying a known force (i.e., stress) in shear and measuring the resulting displacement or strain, the same procedure can be performed in extension (i.e., tension). Hence the extensional Theological properties bear the same relationship to their shear counterparts as the Young's modulus does to the shear modulus in elastic solids. From the filling of shampoo bottles to the manufacture of artificial fibers and the coating of rollers in the printing industry, there is invariably an extensional kinematic component. Extensional kinematics always arise in free surface flows (e.g., in jets, fibers, and sheet drawing processes), or where there is a squeezing mechanism or streamline acceleration. However, most viscometric methods available today for rigorously analyzing fluid properties rely on shear rheometry. Materials that exhibit non-Newtonian material properties, such as a non-linear dependence of viscosity with deformation, typically show complex behavior when they are stretched in a flow, as opposed to sheared. Consequently, shear characterization alone is usually insufficient to fully determine a material's response to the complex flows typically found in industrial processing. Since polymer solutions, melts, and suspensions can have markedly different shear and extensional behavior, this approach can lead to identification of highly misleading parameter values. See, Barnes et al., *An Introduction to Rheology* (Elsevier, Amsterdam, 1989). While current approaches, such as capillary rheometers or falling ball viscometers, provide some indication as to the apparent extensional behavior of materials, these approaches yield data that index, or rank materials, rather than provide absolute quantitative parameters. It is very difficult to follow these approaches and obtain results that are independent of the experimental configuration. In addition, the thermophysical behavior of the fluid in a stretching flow field exposed to ambient conditions (where curing, gelation or mass or heat transfer may occur) may in itself be of interest (for instance in fiber spinning applications). Curing, vitrification, and crystallization all are strongly influenced by the flow field and can be greatly enhanced or retarded in the presence of extensional flows. A technique that can measure relevant material properties for such processes would therefore be invaluable.

Currently there are few other commercially available methods for obtaining data on the extensional behavior of complex fluids (e.g., colloids, adhesives, paints, foods, consumer products, and melts). This paucity of instrumentation is despite increasing academic and industrial interest in measuring the extensional viscosity of a material. Additionally, existing instrument designs are bulky, complex, and expensive. One example of existing commercial extensional rheometers is the RME™ melts rheometer. See, U.S. Pat. No. 3,640,127 and Rheol. Acta., 33, 1–21 (1994). In this instrument, grooved belts stretch a rectangular polymer specimen at temperatures above the polymer's melt temperature while monitoring the force exerted by the specimen.

Another technique is based on atomizing liquids to a measurable particle size in a gas flow. See, U.S. Pat. No. 5,559,284. This technique uses empirical expressions based on known physical properties of the test liquid and atomization conditions to determine the elongation viscosity and surface tension. A small quantity of fluid is stretched between two plates. See, USH0000976 (1991). The stretching is achieved by lowering the bottom plate, which sits on an air cylinder piston. A camera is used to photograph the fluid ligament as it stretches.

A different technique involves extruding a test fluid through a capillary downward into a host fluid, the latter material having a lower density and immiscibility with the test fluid. See, USH0000053 (1986). The drop of test fluid elongates and eventually breaks from the capillary. The extensional viscosity is assessed from photographs of the elongating test fluid drop.

The technique of lubricated flow was used in a converging slit die to determine the extensional viscosity of polymer melts. See, U.S. Pat. No. 5,357,784. In a similar approach, a sample flow is forced through an orifice, thereby affecting an extensional flow. See, U.S. Pat. No. 5,900,539. The extensional viscosity is determined from the flow rate and pressure drop across the orifice.

In U.S. Pat. No. 3,693,425, a filament is wound around a drum while measuring the force on the fixed end of the system. In WO 00728321, a fiber is wound around two drums, one of which measures the torque required to maintain the stretching rate.

Instruments were also developed for extensional characterization of fluids. These systems are based on the filament stretching designs in which a small quantity of fluid is stretched between two plates. See, Vinogradov et al., *J. Polym. Sci., Part A*-2 8, 1–17 (1970) and Münstedt et al., *Rheo. Acta* 20, 211–221 (1981). Data is extracted from these devices through quantitative observations of the evolution of a thin fluid filament under the combined action of viscous, elastic, and capillary forces. Usually both the tension in the filament and the evolution of the diameter are captured. In the original "falling plate" configuration, the sample is subject to a constant load that is imparted by a known weight attached to one of the endplates constraining the sample. See, Matta et al., *Journal of Non-Newtonian Fluid Mechanics* 35, 215–229 (1990). In a filament stretching device, a known exponential displacement profile is imposed and quantitative measurements of the tensile force along the fluid column, $F_z(t)$, and midpoint filament radius, $R_{mid}(t)$, are followed in time. See, Tirtaatmadja et al., *Journal of Rheology* 36, 277–284 (1993) and Spiegelberg et al., *J. Non-Newtonian Fluid Mech.* 64, 229–67 (1996). Extensional flow is of primary interest to industry because almost all processing conditions in manufacturing involve a component of extensional flow. For instance, pumping, fiber spinning, extrusion, molding, and filling processes all involve stretching kinematics. The behavior of all but the simplest materials in such a flow, however, is markedly different from that predicted from knowledge of the shear rheology. Consequently, for process improvement, manufacturing control, and the development and design of materials and components, knowledge of the extensional properties can be critical.

In more recently developed systems, a "necked" liquid bridge configuration is generated by rapidly separating two cylindrical plates a small distance, and the evolution of the midpoint radius, $R_{mid}(t)$, is subsequently followed in time with a non-contact micrometer. Regression of the data leads to the calculation of a Newtonian viscosity or a single mode relaxation time. See, Bazilevsky et al., "Liquid filament Microrheometer and Some of Its Applications," D. R. Oliver, ed., *Proceedings of the Third European Rheology Conference* (Elsevier, 1990), Entov et al., *J. Non-Newtonian Fluid Mech.* 72, 31–53 (1997), and Stelter et al., *Journal of Rheology* 44, 595–616 (2000).

SUMMARY OF THE INVENTION

The apparatus and method described herein generally relate to a capillary breakup rheometer and measurement of rheological properties of a wide spectrum of fluids not accessible with existing instrumentation.

In one aspect, the invention relates to an apparatus for measuring an extensional rheological property of a fluid. The apparatus includes opposed surfaces defining a sample site disposed therebetween, a housing about the sample site, a light source, and a light detector. The opposed surfaces are adapted for axial motion to vary the vertical dimension of the sample site. The housing about the sample site permits specification of ambient conditions. The light source directs a light beam at the sample site. The light detector senses light passing through the sample site.

In another aspect, the invention relates to an apparatus for measuring an extensional rheological property of a fluid. The apparatus includes opposed surfaces defining a sample site disposed therebetween, a plunger assembly, a light source, and a light detector. The opposed surfaces are adapted for axial motion to vary the vertical dimension of the sample site. The plunger assembly allows variation of the vertical dimension of the sample site and variation of the rate of axial movement of at least one of the opposed surfaces. The light source directs a light beam at the sample site. The light detector senses light passing through the sample site.

In yet another aspect, the invention relates to an apparatus for measuring an extensional rheological property of a fluid. The apparatus includes opposed surfaces defining a sample site disposed therebetween, a light source, a light detector, and a data analysis unit. The opposed surfaces are adapted for axial motion to vary the vertical dimension of the sample site. The light source directs a light beam at the sample site. The light detector senses light passing through the sample site. The data analysis unit converts data from the light detector to an extensional rheological property of the fluid sample.

The foregoing and other objects, aspects, features, and advantages of the invention will become more apparent from the following drawings, description, and claims.

BRIEF DESCRIPTION OF THE DRAWINGS

The drawings are not necessarily to scale, emphasis instead is generally placed upon illustrating the principles of the invention to facilitate its understanding.

FIG. 1 is a schematic illustration of an embodiment of an apparatus of the invention.

FIGS. 2*a–h* are images recorded with an apparatus according to one embodiment of the invention.

FIG. 5*a* shows the plunger system in an initial position. FIG. 5*b* shows the plunger system after rotation of the cam.

DETAILED DESCRIPTION

Figure 3A:
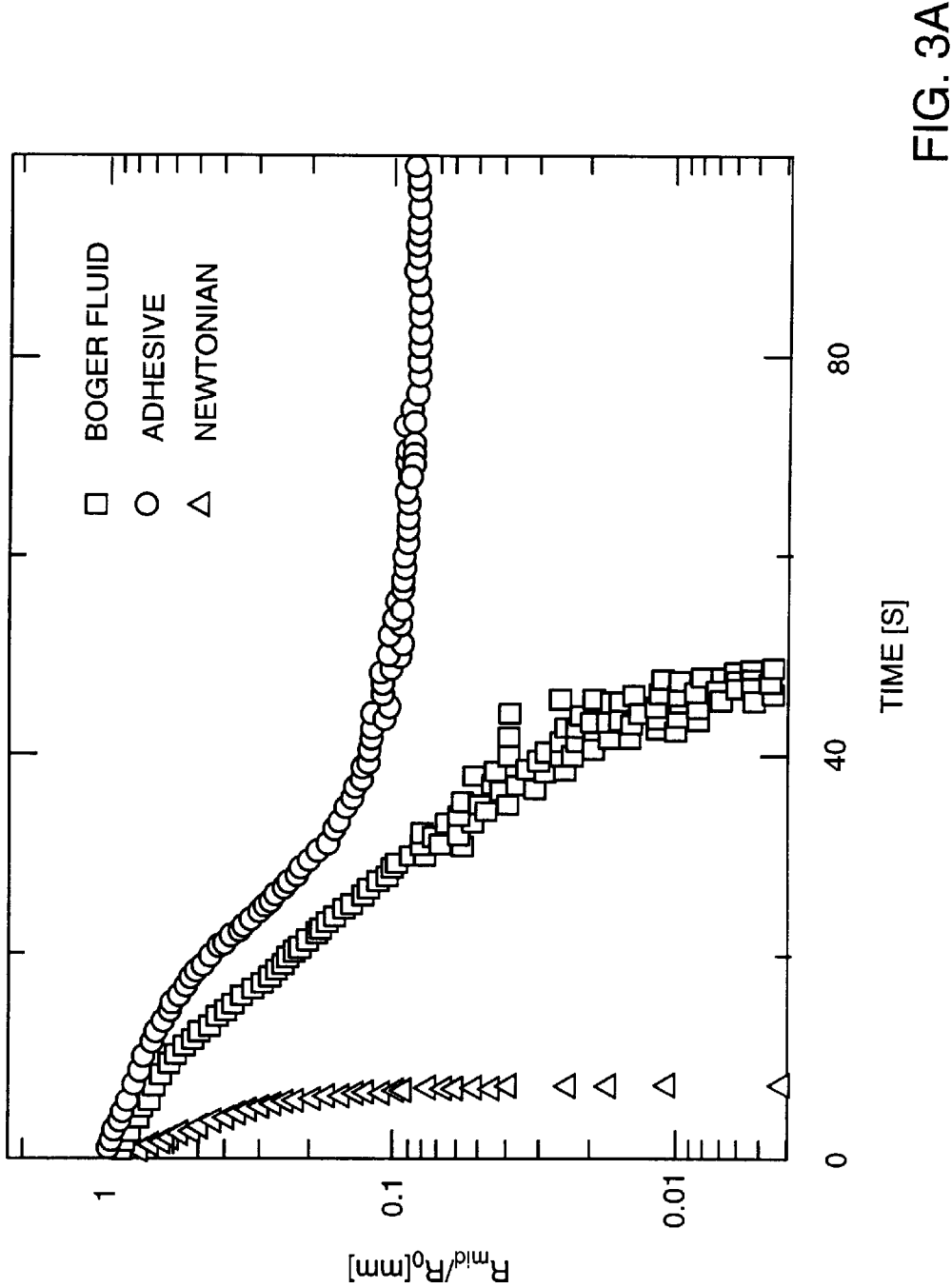
FIGS. 3*a* and 3*b* show plots generated from data collected with an apparatus according to one embodiment of the invention.

Apparatus and methods for measuring extensional rheological properties of materials, e.g., fluids, have been developed. Embodiments of an apparatus of the invention are superior to existing Theological measuring instruments in many respects including, for example, the sophisticated data analytical package; the general applicability of the apparatus (to almost any possible fluid, paste, or melt); the mechanical design enhancements (allowing greater control and repeatability); the control over the sample environment (including temperature, pressure, and humidity); the modular design (allowing easy reconfiguration and optimization); the ability to provide rapid, variable, reproducible, and repeated stretch or reformation; the high resolution time-resolved diameter detection; full image viewing; refined sample loading system; the hand-held unit allowing field analysis; and/or the ability to conduct force measurement and surface tension measurements.

In one aspect, the invention relates to an apparatus for measuring an extensional Theological property of a fluid. The apparatus includes opposed surfaces defining a sample site disposed therebetween, a housing about the sample site, a light source, and a light detector. The opposed surfaces are adapted for axial motion to vary the vertical dimension of the sample site. The housing about the sample site permits specification of ambient conditions. The light source directs a light beam at the sample site. The light detector senses the amount of light occluded by the sample site Referring to FIG. 1, one embodiment of an apparatus 10 includes opposed surfaces 110 and 112, which define a sample site 120. The opposed surfaces 110 and 112 are surfaces at the end of rods 116 and 118. Opposed surface 110 moves axially along axis 160 via a plunger system 170. The sample site 120 is held within a housing 130 which permits controlling ambient conditions. The apparatus further includes a light source 140 which provides a light beam 144. The light beam 144 passes through the sample site 120 and is recorded by a light detector 150. The light detector 150 may be in communication with a data collector such as a personal computer 180 as shown in FIG. 1.

The opposed surfaces may be surfaces on a pair of opposing plates or rods. When the opposed surfaces are opposing plates, the plates may be connected to rods or other structure which permits axial motion to vary the vertical dimension of the sample site. The shape of the opposed surfaces are not limited to a particular shape and may be circular, square, rectangle, or other geometries. The opposed surfaces are generally parallel to each other during measurement, but need not be so, as other configurations may be preferred in certain applications. The size of the opposed surfaces is not limited. In general, the area of the opposed surfaces can be in a wide range depending upon the application and the design of the apparatus. In addition, the opposed surfaces may be of different sizes and shape. In one embodiment, the opposed surfaces are surfaces of a pair of plates. The plates may be interchangeable. The opposed surfaces may be circular. The diameter of circular opposed surfaces can range from about 10 $\mu$m to about 1 cm. In one embodiment, the diameter ranges from about 10 $\mu$m to about 1 mm. In another embodiment, the diameter ranges from about 1 mm to about 5 mm. In yet another embodiment, the diameter ranges from about 5 mm to about 1 cm.

The surfaces may be constructed of any material. Illustrative materials include, but are not limited to, aluminum, stainless steel, Delrin, polyethylene, glass, and polytetrafluoroethylene. The surfaces can have end shapes other than flat (e.g., spherical or conical). The surfaces may be polished, roughened, or chemically-coated to ensure good adhesion between the fluid sample and the opposed surfaces. Alternatively, the physical and chemical nature of the plate surfaces can be modified to examine the wetting and/or de-adhesion characteristics of the sample material during extension.

The sample site is defined by the opposed surfaces; therefore, its actual size and shape depend on the selection and positioning of the opposed surfaces. The sample site may sit inside a sample housing (or an environmental chamber), which can provide control over the temperature, humidity, and pressure inside in the sample housing. Since the rheological behavior of fluids and melts is generally very sensitive to temperature, accurate temperature control can be critical.

Accordingly, referring to FIG. 1, the apparatus 10 may include a heating system 134, e.g., an oven, and a temperature controller 136 that are capable of providing control over the temperature of the sample site 120 and the environment surrounding the sample site. The heating system typically is used to maintain a temperature from about ambient temperature up to about 400° C. The temperature controller 136 can monitor the temperature and appropriately adjust the power to the heating system to reach and maintain the desired setpoint. For sub-ambient temperature control down to about −150° C., a cooler 138 (thermoelectric or circulating cold nitrogen gas or liquid) may be used. Other temperature control methods and devices may be used, including, but not limited to, convection heating, induction heating, and thermoelectric coolers. Additional environmental control, including relative humidity (0–99% RH) and partial pressure of gases, may be achieved by circulating conditioned gas into and out of the sample housing of the apparatus (not shown). Alternatively or in conjunction therewith, salt baths placed in the sample housing may be used to control relative humidity. Solvent partial pressure could be achieved by placing solvent in trays inside the sample housing. External or internal sensors may be used to monitor the sample housing's atmosphere. A heating system, an oven, a temperature controller, a cooler, and/or any other environmental control system may be modular in design to permit field installation.

The apparatus depicted in FIG. 1 is a filament breakup rheometer. The fluid sample is placed at the sample site having contact with both opposed surfaces. One or both opposed surfaces undergo a vertical motion resulting in a stretching of the fluid sample between the opposed surfaces. The liquid sample undergoes an extensional deformation between the opposed surfaces which separate at a prescribed rate. A liquid filament is formed as the liquid sample is stretched. The diameter of the filament decreases as it is under the competitive influences including surface tension, elasticity, viscosity, mass transfer, and gravity. The time profile of the diameter of the liquid filament is monitored and recorded as a function of time. Analysis of the time profile provides information about the extensional viscosity as a function of strain, surface tension, elasticity, yield stress, breakup time, and other parameters.

The motion of the opposed surfaces can be either a step strain or a user-defined velocity profile to the final level of strain. For example, the step strain can be achieved by releasing a spring-activated plunger assembly. Both the initial and final aspect ratios, defined as the ratio of the sample length to the sample radius, may be adjusted by the user. As with other movement of structure of the apparatus, computer control may be used to direct the motion of the opposed surface or surfaces. Computer control can provide reproducibility and the capability of readily implementing user-defined motion profiles, as well as the ability to automate portions or entire methods of the invention.

The light source provides a light beam which passes through the sample site. The light beam is received and recorded by a light detector. The light source may be a coherent or incoherent light source. The light source may be monochromic or multichromic. One or more filters may be used for certain applications where the wavelength and/or intensity of the light beam need to be manipulated. In one embodiment of the invention, the light source may be a laser that emits a laser beam directed at the sample site. In another embodiment, the light source is a laser micrometer transmitter.

The light detector may be anything that allows recording of the light beam transmitted through the sample site. The light detector may be a still camera or a video camera. When a camera is used, it is focused on the filament (124 in FIG. 1) to monitor the full filament profile during the filament's breakup. In one embodiment, the light detector fully visualizes the filament during initial extensional deformation and stretching, and during relaxation and sample breakup. The camera collects images frame by frame and allows thresholding and extraction of the x-y coordinates of the edges of the filament. The images may be digitized so that subsequent computer analysis and/or manipulation of the images can provide filament contours and other useful information, such as radius of curvature as a function of position. The images and associated information also may be used for a variety of other purposes including, for example: (1) model simulation; (2) extraction of information about gravitational effects; (3) determination of the quality of the stretch through highlighting problems with sample loading, the presence of bubbles, or other perturbative factors; and (4) enhancement of the understanding of the breakup mechanism itself. The camera can be a charge-coupled device (CCD), infrared, digital camera, 35 mm, or other imaging technology used by those skilled in the art.

In another embodiment, the light detector is a laser micrometer receiver. A laser micrometer receiver or other noncontact diameter sensing device monitors the diameter of the filament as a function of time during and after the stretching deformation. The micrometer is placed so that it intersects the midpoint (126 in FIG. 1) of the filament after stretching. Likewise, images of the deforming filament taken with a digital, analog, or film camera can be collected, digitized if necessary, and analyzed to obtain, e.g., the diameter as a function of position and time.

A laser micrometer system provides advantages in at least three important respects. The response time is usually very fast due to the requirement for high throughputs in production line monitoring. Designed using infrared light and run in a "chopped" mode, such a system is immune to ambient lighting conditions. The resolution of the laser micrometer may be in a range of from around 1 $\mu$m to about 100 $\mu$m. Multiple micrometers can also be used to monitor the diameter history at several positions in the filament. The micrometers can be placed circumferentially around the filament, or stacked on one side. To improve the lower end resolution, where the filament diameter is less than 10 $\mu$m, magnifying lenses can be used to effectively increase the gain of the micrometer. In one embodiment, the laser micrometer system has a response time of about 0.1 ms to about 100 ms.

Figure 3B:
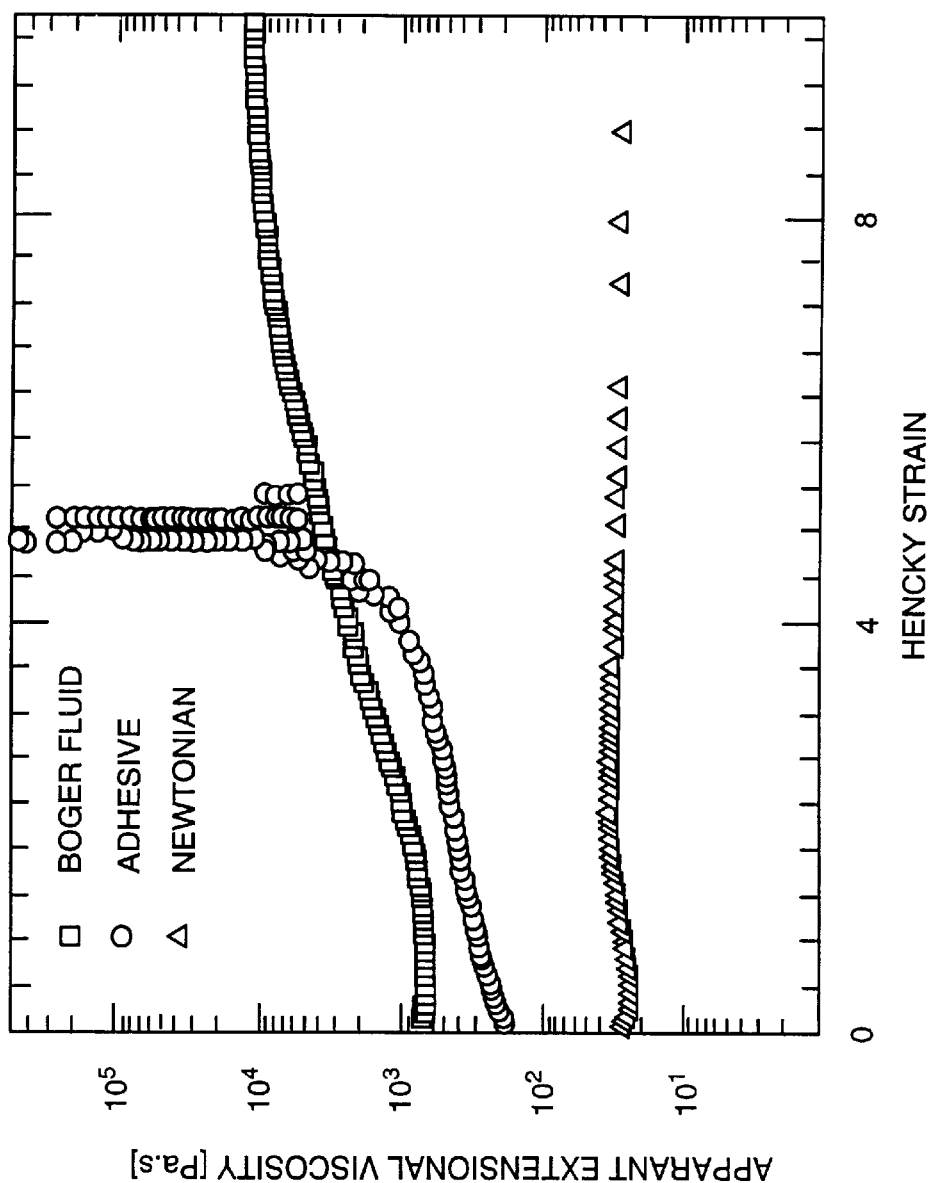

Examples of images depicting the breakup of sample fluids recorded using an apparatus of the invention are shown in FIGS. 2a–h. FIGS. 2a–d are a sequence of time-lapsed images where the sample is a styrene oligomer, a simple Newtonian fluid that is dominated by viscous forces. FIGS. 2e–h are a sequence of time-lapsed images where the sample is the same oligomer with a dilute (500 ppm) high molecular weight polystyrene molecule added. This solution is a model elastic fluid known as a "Boger Fluid" that strongly strain-hardens in extension (See, Spiegelberg et al., *J. Non-Newtonian Fluid Mechanics*, 64, 229 (1996)). Visually there is a clear difference between the two samples even though their shear viscosity is virtually identical. The evolution versus time of the mid-point diameter measured with the apparatus of the invention is plotted in FIG. 3a which contains three sets of data showing normalized filament radius versus time. The data are for three fluids, the simple Newtonian fluid and the model elastic fluid ("Boger Fluid") of FIGS. 2a–d and 2e–h, respectively, and a pressure sensitive adhesive. FIG. 3b shows apparent extensional viscosity versus strain calculated from the data of FIG. 3a using a software package described herein below. The difference between the extension of the two fluids is clearly shown. For comparison, a third set of data for a pressure sensitive adhesive is also plotted.

Again referring to FIG. 1, one or both of the opposed surfaces 110 and 112 may be adapted for axial motion (along axis 160) to vary the vertical dimension of the sample site 120. The controlling of the axial movement of the opposed surfaces 110 and 112 may be by way of a plunger system 170. The plunger system 170 may be of any configuration as long as the desired motion profile of the controlled surface is achieved. In one embodiment, the desired initial deformation is achieved by a rapid extensional step-strain. In other embodiments, the plunger system includes a variable speed drive which is capable of producing position versus time profiles that are linear, exponential, constant, or according to a user-defined profile. Further, the plunger system may be run in batch mode to test multiple samples or to test the same sample repeatedly.

Figure 4:
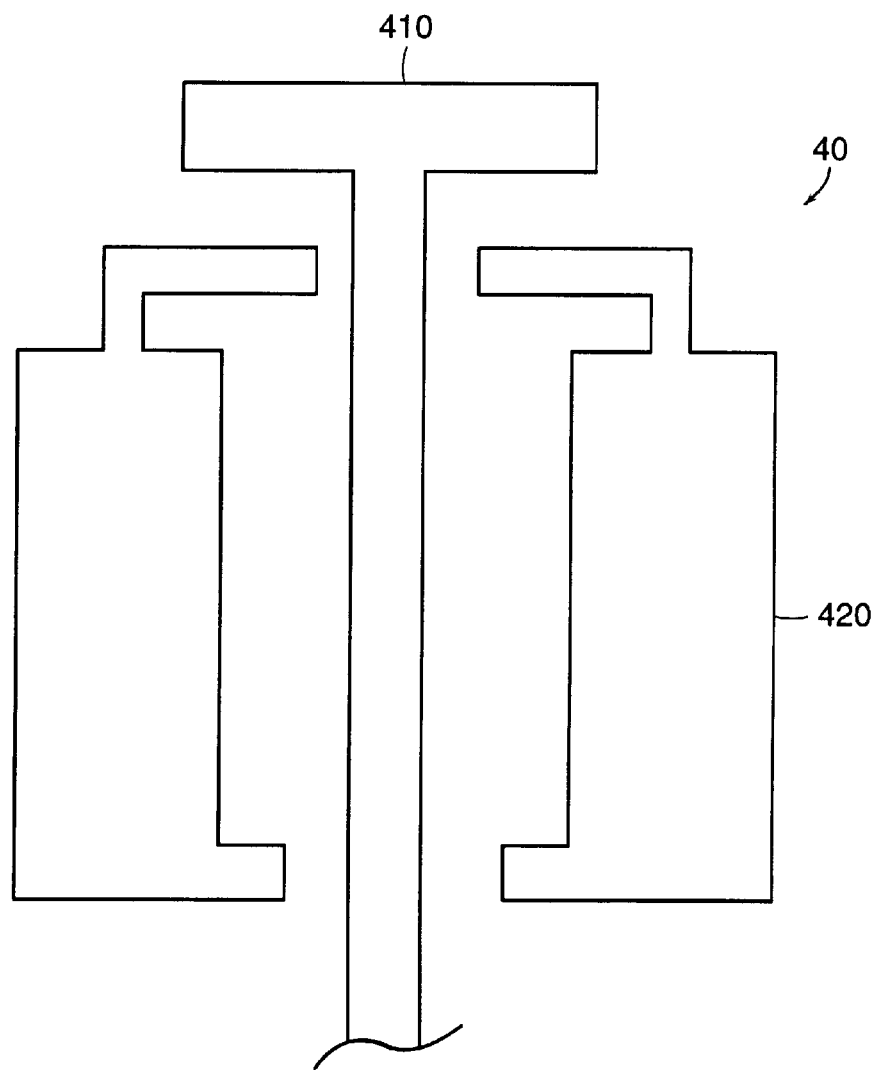
FIG. 4 is a schematic side cross-sectional illustration of an embodiment of a solenoid-driven plunger system that may be used in an embodiment of an apparatus of the invention.

Referring to FIG. 4, a solenoid-driven plunger system 40 may be used in an apparatus of the invention to provide axial motion of one or both of the opposed surfaces. The solenoid-driven plunger system includes a plunger 410 mounted in a hollow cylinder 420. A spring (not shown) may be included and connected to the plunger 410 to modify its motion profile. The solenoid-driven plunger system allows the initial and final gaps (e.g., the vertical dimension of the sample site) to be adjusted independently to control the total strain and initial aspect ratio. Inclusion of a spring lock allows changing of the spring and adjustment of the pre-tension on the spring, thereby achieving control over the stretch rate.

Figures 5A, 5B:
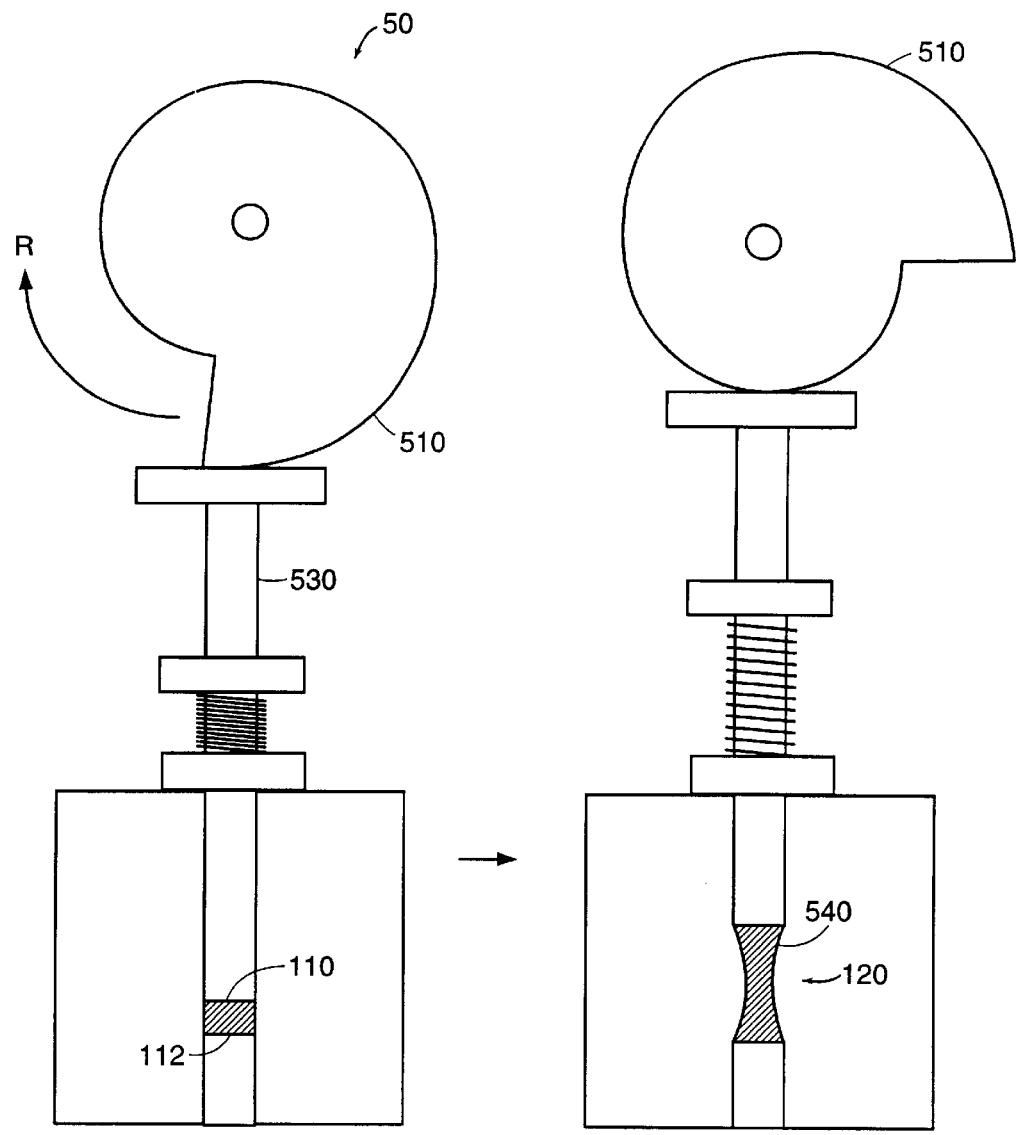
FIGS. 5*a–b* are schematic illustrations of an embodiment of a cam-driven plunger system that may be used in an embodiment of an apparatus of the invention.

Referring to FIG. 5a, the plunger system may be a cam-driven plunger system 50. The cam-driven plunger system 50 employs a cam 510 which may be driven by various means, e.g., by manual force or by a motor. The profile of the cam and its speed of rotation determines the motion profile of the plunger 530 and consequently, the motion profile of one of the opposed surfaces (110 in FIG. 5a). FIG. 5b shows the cam-driven plunger system 50 after rotation of the cam 510 in the direction of the curved arrow pointing towards the letter "R." FIG. 5b shows a stretched fluid sample 540, e.g., a liquid filament, located in the sample site 120. Note that the cam-driven plunger system may include two cams for controlling the motion of both opposed surfaces. Both the profile of the cam and its speed of rotation can be designed to achieve the desired motion profile of the opposed surface to which it is in communication. For example, the cam may be constructed to have an exponentially-increasing radius. The cam could also be machined to provide other required deformation histories, including but not limited to, power law, linear, and logarithmic.

Variable speed drive systems may be constructed out of other linear motion technologies including, but not limited to, linear motors, rolling ring drives, belt drives, pneumatic actuators, damped spring drives, and ball screw drives. The drive motor may be designed to release the plunger at a controlled rate upon a specification of a strain rate. This approach is particularly useful for materials that exhibit association times, such as surfactant systems. Strain rates may vary from about 0.001 $sec^{-1}$ to about 1000 $sec^{-1}$. This range of rates can be achieved with a single motor, or with interchangeable motors. In one embodiment, the strain rates are within a range from about 0.001 $sec^{-1}$ to about 1.0 $sec^{-1}$. In another embodiment, the strain rates are within a range from about 1.0 $sec^{-1}$ to about 1000 $sec^{-1}$.

Figure 6:
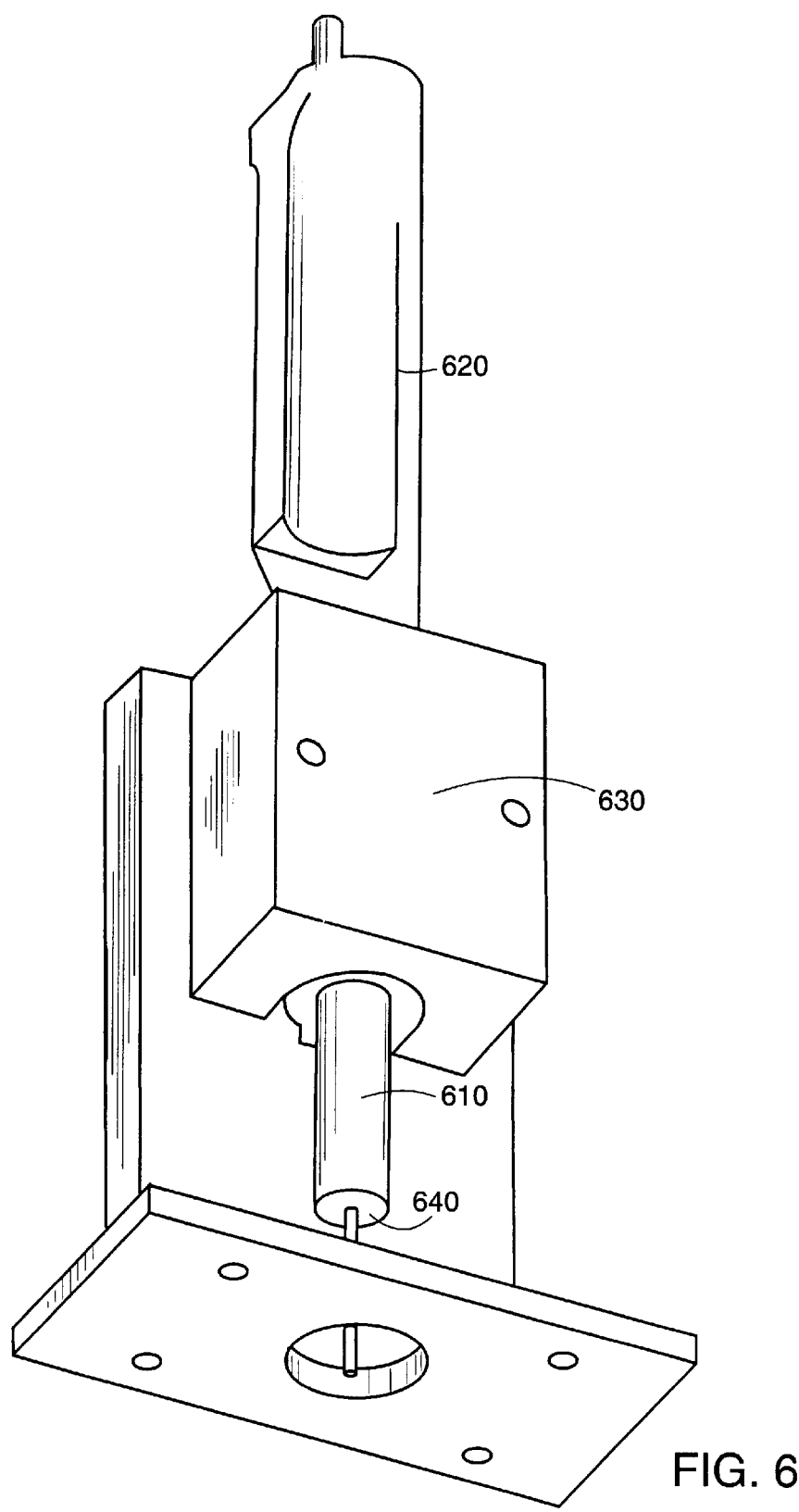
FIG. 6 is a schematic illustration of an embodiment of a plunger system of the invention which is a linear drive system.

In one embodiment, the entire plunger assembly may be replaced with a linear drive motor system. An example of a linear drive motor system is shown in FIG. 6. A motor core 610 is free to move within a motor assembly 620. The motor assembly 620 is attached to a mount 630 that allows the motor core 610 to move axially, e.g., vertically, in the apparatus. A top plate of the system 640 is attached directly to the core 610. A linear drive motor system allows user-defined motion profiles, variation of the velocity of an opposed surface as a function of time, and easy specification of the total length of the stretch.

Repeated stretching of samples can be achieved with the above systems. In one embodiment, the drive system is constructed to allow repeated stretching of the same fluid specimen, with user-defined relaxation times, stretch rates, and stretch times.

The apparatus may further include a sample loading device. The sample loading device introduces a sample to the sample site, e.g., via a syringe-type delivery system. The syringe-type delivery system may be manually-driven, air-driven, or mechanically-actuated.

Figure 7:
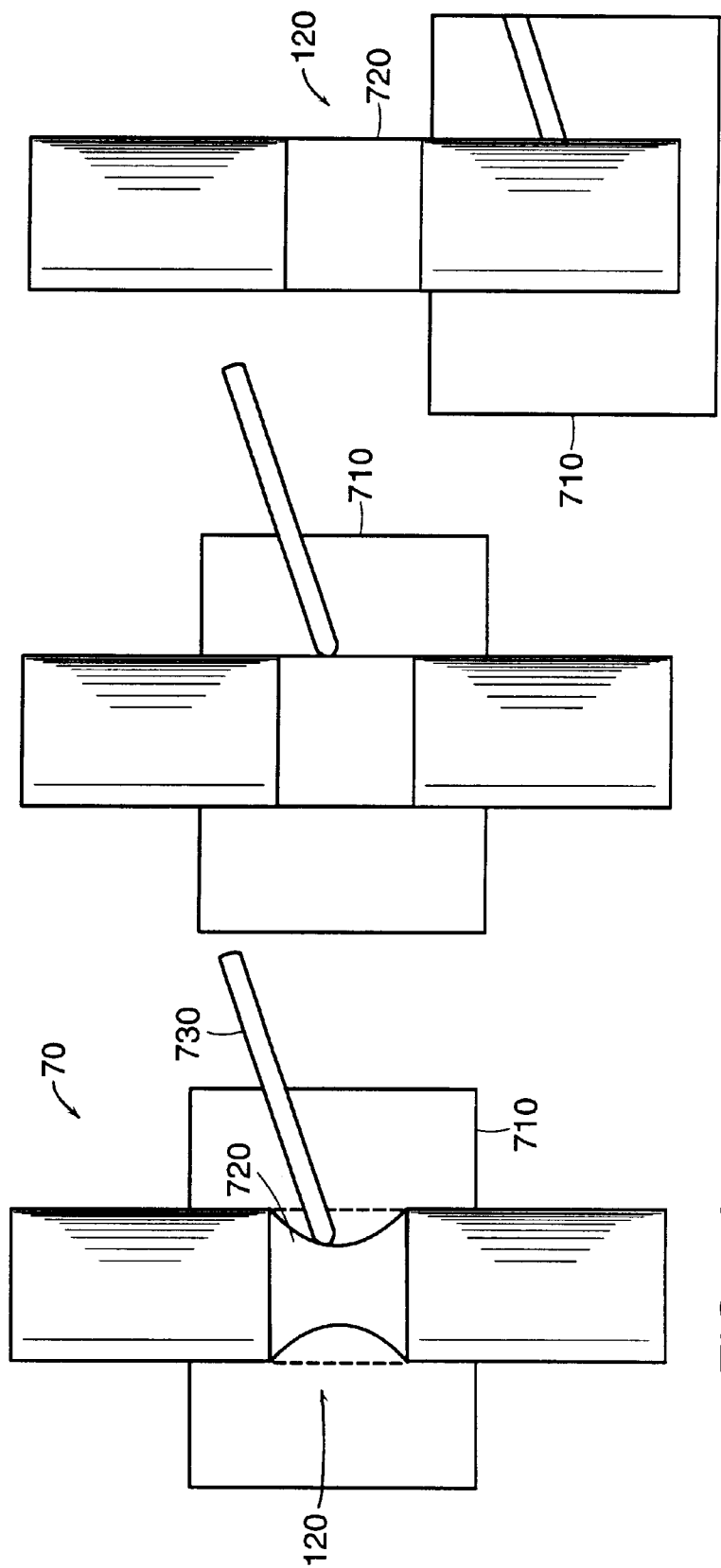
FIGS. 7*a–c* are illustrations of embodiments of a sample loading system that may be used in an embodiment of an apparatus of the invention.

FIGS. 7a–c depict an embodiment of a sample loading device, i.e., a moveable sleeve system 70, which is useful for measuring volatile materials. A sleeve 710 is positioned about the sample site 120 to define and typically isolate it. A fluid sample 720 is injected into the sample site 120 e.g., via a syringe needle 730. The fluid sample 720 is allowed to relax, immune to environmental affects as shown in FIG. 7b. In FIG. 7c, the sleeve 710 is removed, e.g., by sliding, to expose the sample 720 in the sample site 120 prior to stretching. The sliding motion can be achieved manually, using spring-actuation, or via a motor drive. The sleeve may be constructed from most any material including, but not limited to, stainless steel, acrylic, polytetrafluoroethylene, Delrin, aluminum, polyethylene, polycarbonate. The sleeve and the opposed surfaces may be pre-treated with surfactant, cleaning agents, or other treatments used by those skilled in the art.

Figure 8:
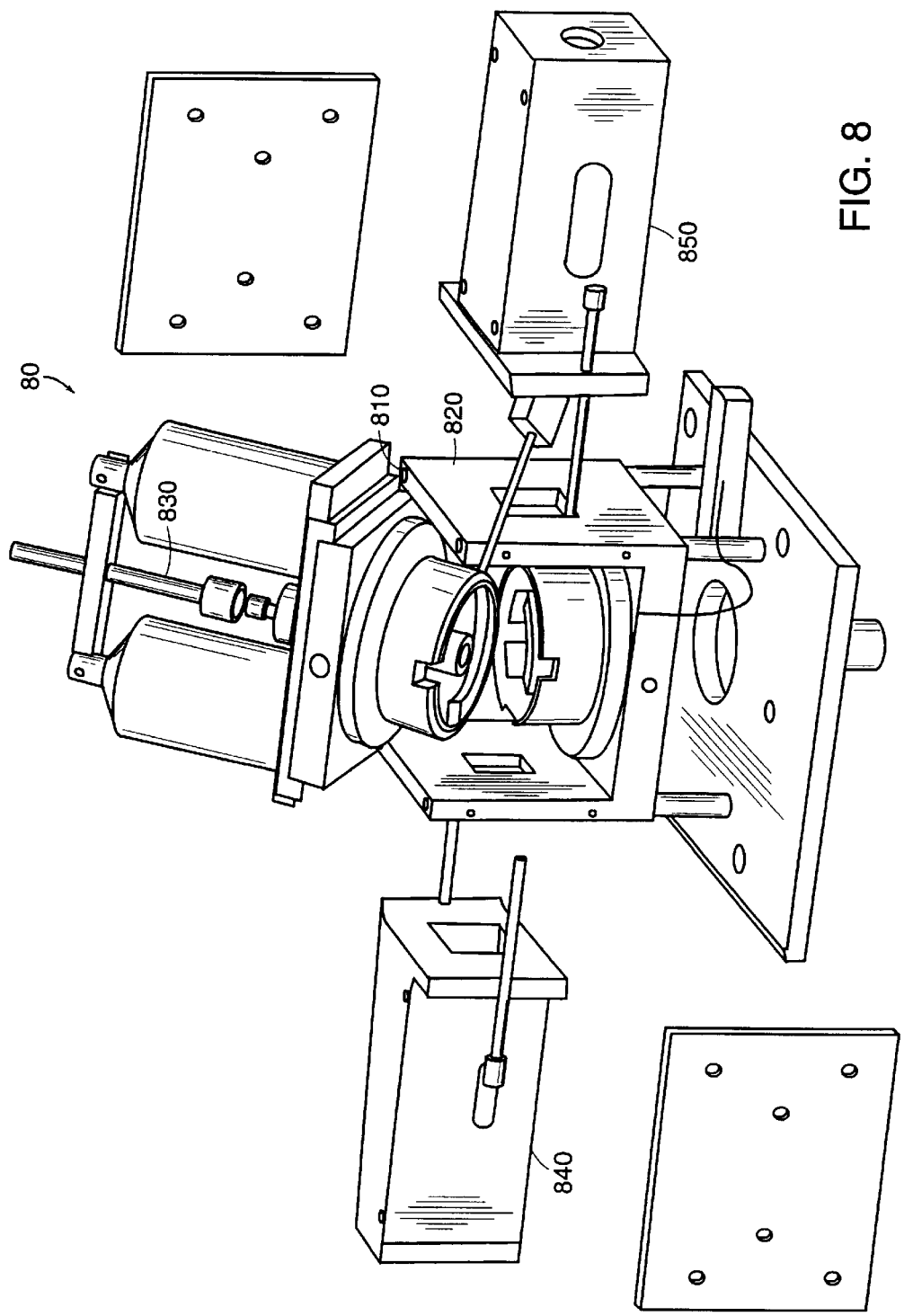
FIG. 8 is a schematic illustration of a modular design of one embodiment of an apparatus of the invention.

As shown in FIG. 8, an apparatus of the invention 80 readily conforms to a modular design which allows easy reconfiguration, optimization, and maintenance. For example, a hinge 810 allows easy sample change-out and cleaning. The housing 820 can be removed and immersed in a solvent or other cleaning agent, or cleaned in an ultrasonic bath. Likewise, sample plates (not shown) can be individually removed for cleaning and/or pre-treatment. The height and stroke of a spring loaded plunger 830 can be independently adjusted. It should be understood that the plunger drive system can be exchanged with any suitable drive system, and can be field-installed. The laser micrometers, i.e., the laser micrometer transmitter 840 and the laser micrometer receiver 850, can be moved to provide access for optional cameras.

Figure 9:
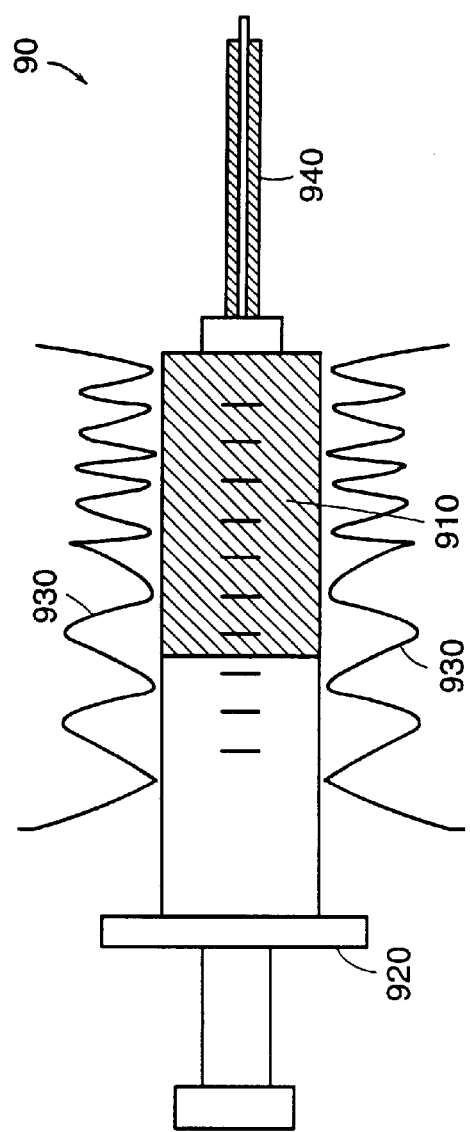
FIG. 9 is a schematic illustration of an embodiment of a sample loading system that may be used in an embodiment of an apparatus of the invention.

Samples that need to be tested at elevated temperatures can be injected through a heated syringe system. FIG. 9 shows an embodiment of a heated syringe system 90. A sample 910 (e.g., a solid, a granular, or a powder) can be loaded in a syringe 920. The syringe 920 may be evacuated to reduce or eliminate oxygen, and/or backfilled with an inert or sensitizing gas such as argon, nitrogen, or helium. The syringe 920 (or the whole syringe system 90 plus the opposed surfaces) may be heated to the desired temperature by using a heated jacket (not shown) or heating coils 930 connected to an electrical heater and/or a temperature controller (not shown). The heated syringe system 90 may also include an insulated needle 940 as shown in FIG. 9. After the sample 910 is liquefied, it may be loaded onto the heated opposed surfaces of the sample site.

Figure 10:
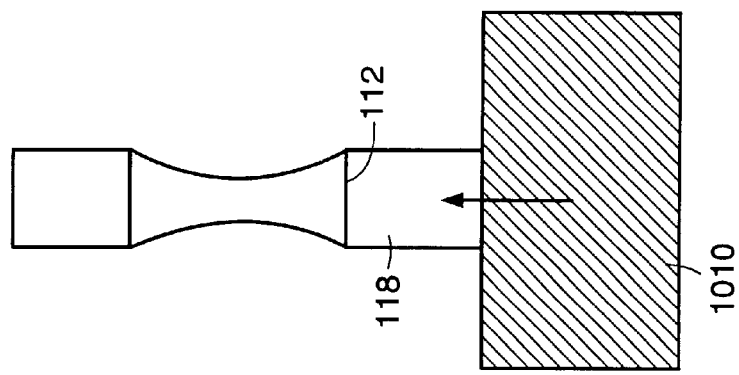
FIG. 10 is a schematic illustration of an embodiment of a force transducer in communication with an opposed surface of the invention.

A force transducer may be in direct or indirect contact with one (e.g., the bottom) or both opposed surfaces. The force transducer permits the measurement of the transient tensile force during the initial extensional deformation and stretch, and during relaxation and sample breakup. The force transducer may be integrated with the bottom plate. Referring to FIG. 10, a force transducer 1010 is attached to the bottom of rod 118 whose end is an opposed surface 112. The force transducer may have a dynamic range from about 1 dyne to about 100,000 dynes. In one embodiment, the force transducer has a dynamic range from about 1 dyne to about 10,000 dynes. In another embodiment, the force transducer may have a dynamic range from about 10,000 dyne to about 100,000 dynes. The response time of the force transducer is about 50 ms or less, with a preferred response time of about 1 ms. In one embodiment, the response time of the force transducer is about 25 ms or less. In another embodiment, the response time of the force transducer is about 10 ms or less. Dual range force transducers or interchangeable force transducers may be used, depending on the force range required. The desired force range is from about 10 $\mu$N to about 1 N. In one embodiment, the force range is from about 10 $\mu$N to about 0.1 N. In another embodiment, the force range is from about 0.1 N to about 1 N.

The apparatus of the invention may be of a dimension and geometry such that it is portable and can be hand-held. Field measurements of the rheological properties of fluids and melts may be necessary for quality assurance testing. FIG. 11a shows an example of a hand-held apparatus 111 that includes an on-board data logger (not shown) located inside a handle 1110 of the apparatus 111. The handle 1110 includes appropriate ports and connections, e.g., a computer cable 1120, for communicating the on-board data logger with another data processing device, e.g., an external computer (not shown). The on-board data logger may be directly connected to a computer during the analysis of samples or may be downloaded to a computer at a later time. The handle 1110 also is in communication with the body 1130 of the hand-held apparatus. The body 1130 contains the mechanical and optical components described above necessary for the measurement of the rheological properties of a sample. It should be understood that many variations to the design of an apparatus of the invention are possible and within the skill in the art.

Figure 11D:
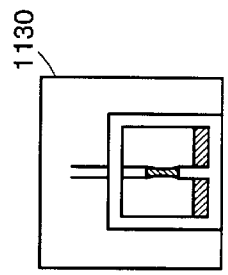
FIGS. 11*b–d* show an example of the operation of a hand-held apparatus of the invention.
Figure 11A:
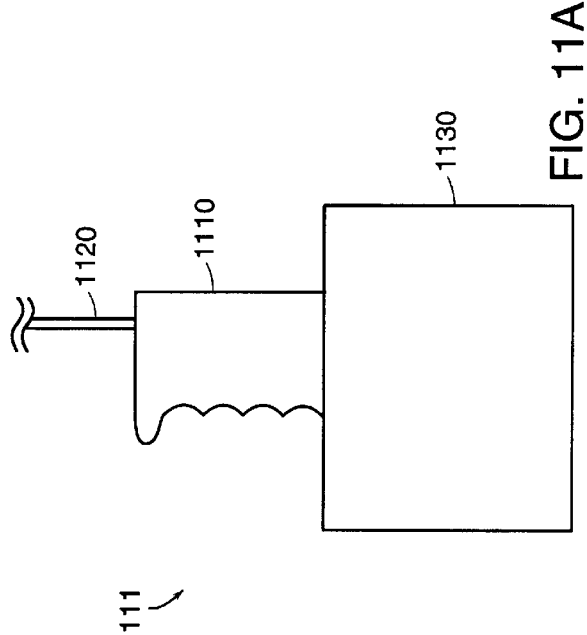
FIG. 11*a* is a schematic illustration of an embodiment of a hand-held apparatus of the invention.
Figure 11C:
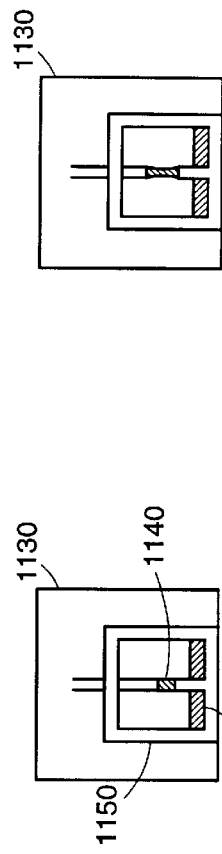
Figure 11B:
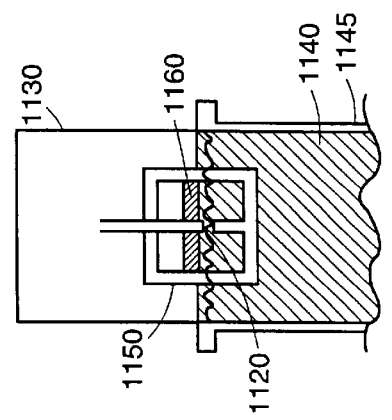

FIGS. 11b–d show an example of a hand-held apparatus in operation (note that FIGS. 11 b–d depict the body 1130 of the hand-held apparatus without its handle 1110 or other peripheral components, e.g., a computer cable 1120). In operation, as shown in FIG. 11b, a test fluid 1140 is introduced into the sample site 120 by extending a probe 1150 from the body 1130 of the apparatus into a container 1145 of the test fluid 1140. The test fluid 1140 is permitted to fill the sample site 120, then as shown in FIG. 11c, the probe 1150 is retracted into the body 1130 of the apparatus past a scraper 1160 which cleans the sample site 120 to provide a reproducible sample for analysis. In FIG. 5d, the test fluid 1140 is stretched and analyzed as described above, e.g., the history of the diameter at the mid-point of the stretched fluid may be recorded. The hand-held apparatus 111 can provide the breakup time or other simple parameters on site. More detailed data analysis may be performed, on site or afterwards, after downloading the data to the host computer that contains the full software analysis package. Level indicators may be included to allow the user to hold the hand-held apparatus normal to gravity, as is the direction of the stretching.

Software Design

A number of authors have published work relating to the breakup dynamics of a fluid filament. See, Bazilevsky et al., *Liquid Filament Microrheometer and Some of Its Applications*, D. R. Oliver, ed., *Proceedings of the Third European Rheology Conference* (Elsevier, 1990); Stelter et al., *Journal of Rheology* 44, 595–616 (2000); Bazilevsky et al., *Polym. Sci., Ser. A* 39, 316–324 (1997); Liang et al., *Journal of Non-Newtonian Fluid Mechanics* 52, 387–405 (1994); and McKinley et al., *Journal of Rheology* 44 (2000). Academic research in this area has focused principally on model fluids (e.g., constant viscosity Newtonian oils and dilute homopolymer solutions) that can be described by simple constitutive models such as the Maxwell model. This restriction on the choice of test materials facilitates extraction of material properties since the dynamics of the capillary thinning are simple enough to be analyzed quantitatively. However, it clearly constrains the commercial viability of such a device. A framework of a systematic approach to the analysis of an arbitrary test fluid, whose extensional viscoelastic properties are unknown a priori, is described below.

Newtonian Fluids

In a filament rheometer, the sample is constrained axially between two smooth coaxial disks of radius $R_0$ and forms a liquid bridge configuration that is nominally cylindrical in shape. The precise shape is determined by satisfying the Young-Laplace equation and is a function of the aspect ratio $\Lambda_0=2L_0/D_0$, the volume of fluid contained between the plates and the gravitational body force and surface tension. See, McKinley et al., *Journal of Rheology* 44 (2000); Slobozhanin et al., *Physics of Fluids A* 5, 1305–1314 (1993); and Szabo, *Rheologica Acta* 36, 277–284 (1997).

In a capillary breakup rheometer, the plates are separated rapidly over a short distance. In this respect, the device functions as the extensional equivalent of the step-strain test in conventional rheometry. A liquid bridge is therefore generated which has a distinctly necked but axisymmetric configuration. Once this new, unstable necked configuration has been established, the midpoint diameter $D_{mid}(t)$ is monitored as a function of time using a laser micrometer (or by some other sensing device/technique). If inertial effects and viscous stresses in the external fluid are negligible, this necked configuration is symmetric about the midplane. If inertial effects and viscous stresses in the external fluid are significant, more complex shapes can arise. See, Berg et al., *Journal of Non-Newtonian Fluid Mechanics* 55, 307–319 (1994) and Gaudet et al., *Physics of Fluids* 8, 2568–2579 (1996).

Figure 12:
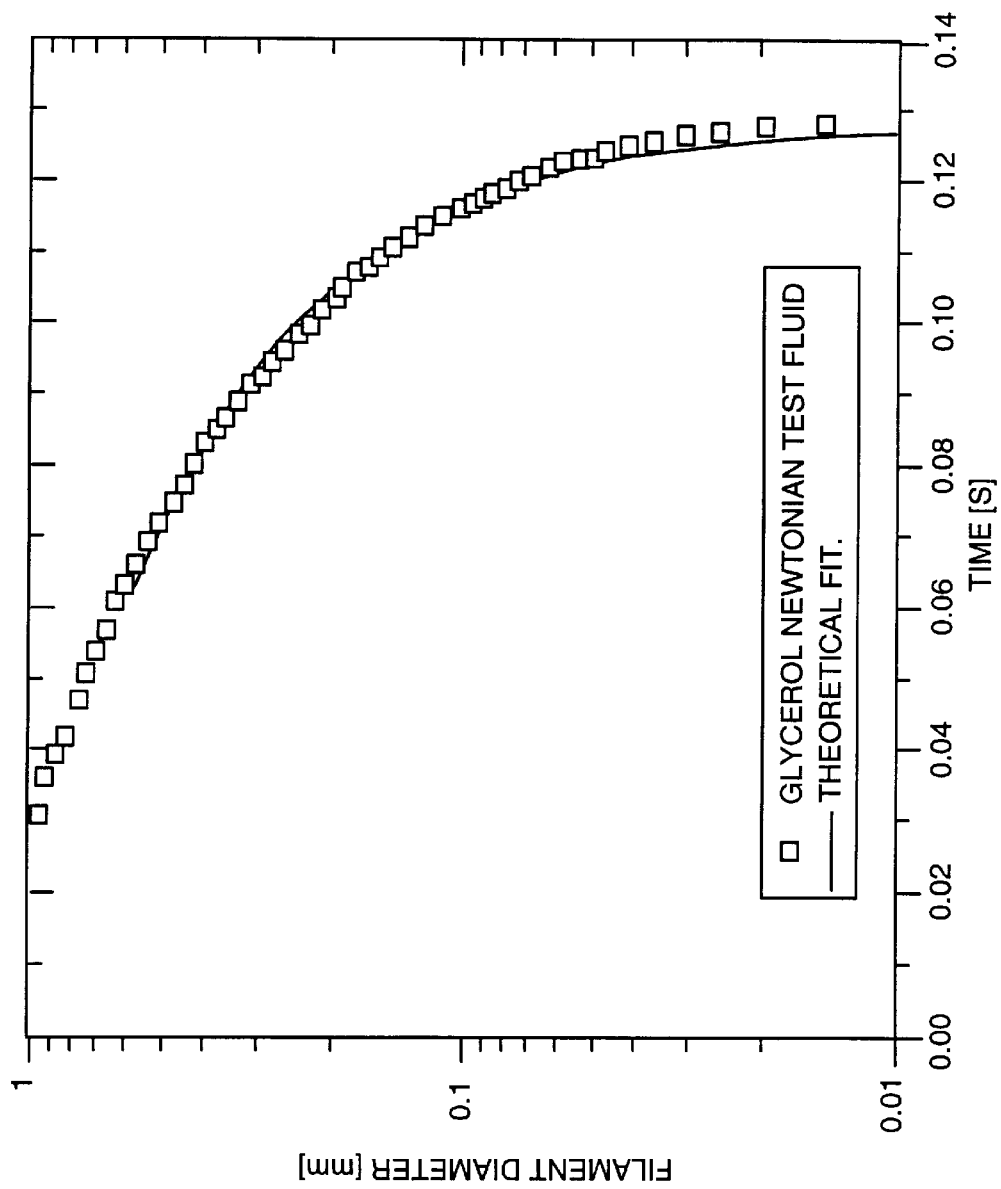
FIG. 12 shows a plot generated from data collected with an apparatus according to one embodiment of the invention.

The dynamics of the drainage of the thin fluid column and the ultimate rupture of the liquid bridge into two or more droplets are governed by the viscous and elastic properties of the fluid. See, Eggers, *Review of Modern Physics* 69, 865–929 (1997). Detailed theoretical analysis and numerical simulations using a slender body theory shows that the time evolution of the midpoint diameter of a Newtonian fluid can always be described by the following equation:

$$D_{mid}(t) = D_1 - \frac{(2X(t)-1)}{3}\frac{\sigma}{\eta_s}t \qquad (1)$$

where the non-local effects arising from axial variations in the shape of the filament are encoded in the net tensile force F(t) acting on the filament thread. See, McKinley et al., *Journal of Rheology* 44 (2000). These effects appear in equation (1) through the dimensionless function $X(t)=F(t)/\pi\sigma D_{mid}(t)$. Correct determination of the function X(t) allows the calculation of the ratio $\sigma/\eta_s$. If an experiment is performed and the midpoint diameter $D_{mid}(t)$ is indeed found to decrease linearly in time, then the value of the ratio $\sigma/\eta_s$ determined from regression of the data will depend critically on what appropriate value of X to use in the analysis. The experimental results analyzed elsewhere have all assumed implicitly that X=1. See Bazilevsky et al., "Liquid Filament Microrheometer and Some of Its Applications," D. R. Oliver, Ed., *Proceedings of the Third European Rheology Conference* (Elsevier, 1990); Kolte et al., *Journal of Rheology* 43, 609–626 (1999); and Liang et al., *Journal of Non-Newtonian Fluid Mechanics* 52, 387–405 (1994). However, it has recently been pointed out that for typical experimental conditions, the most appropriate value is actually X=0.7127, in accordance with the self-similar solution of Papageorgiou. See, McKinley et al., *Journal of Rheology* 44 (2000) and Papageorgiou, *Physics of Fluids* 7, 1529–1544 (1995). To date, published experimental work has assumed that X=1. The published estimates for the extensional viscosity have all been incorrectly scaled by a factor of approximately 2. FIG. 12 shows data on a semi-logarithmic scale fitted using X=0.7127. FIG. 12 shows a glycerol fluid at room temperature with aNewtonian fit overlaid. The fit yields a capillary velocity of $\sigma/\eta=16.5$ m/s. Using the known surface tension of glycerol, $\sigma=64.8$ mN/m, a viscosity of 1.07 Pa.s is calculated compared to an accepted literature value of $\eta=1.03$ Pa.s. For a simple Newtonian model fluid the capillary breakup rheometer allows the extraction of a characteristic ratio, $\sigma/\eta_s$, that fully defines the fluid. The units for this ratio, $\sigma/\eta_s$, are meters per second (m/s). This parameter is identified as the characteristic "capillary velocity" of the fluid, which describes the rate of thinning in a viscous fluid.

Elastic Fluids

Figure 13:
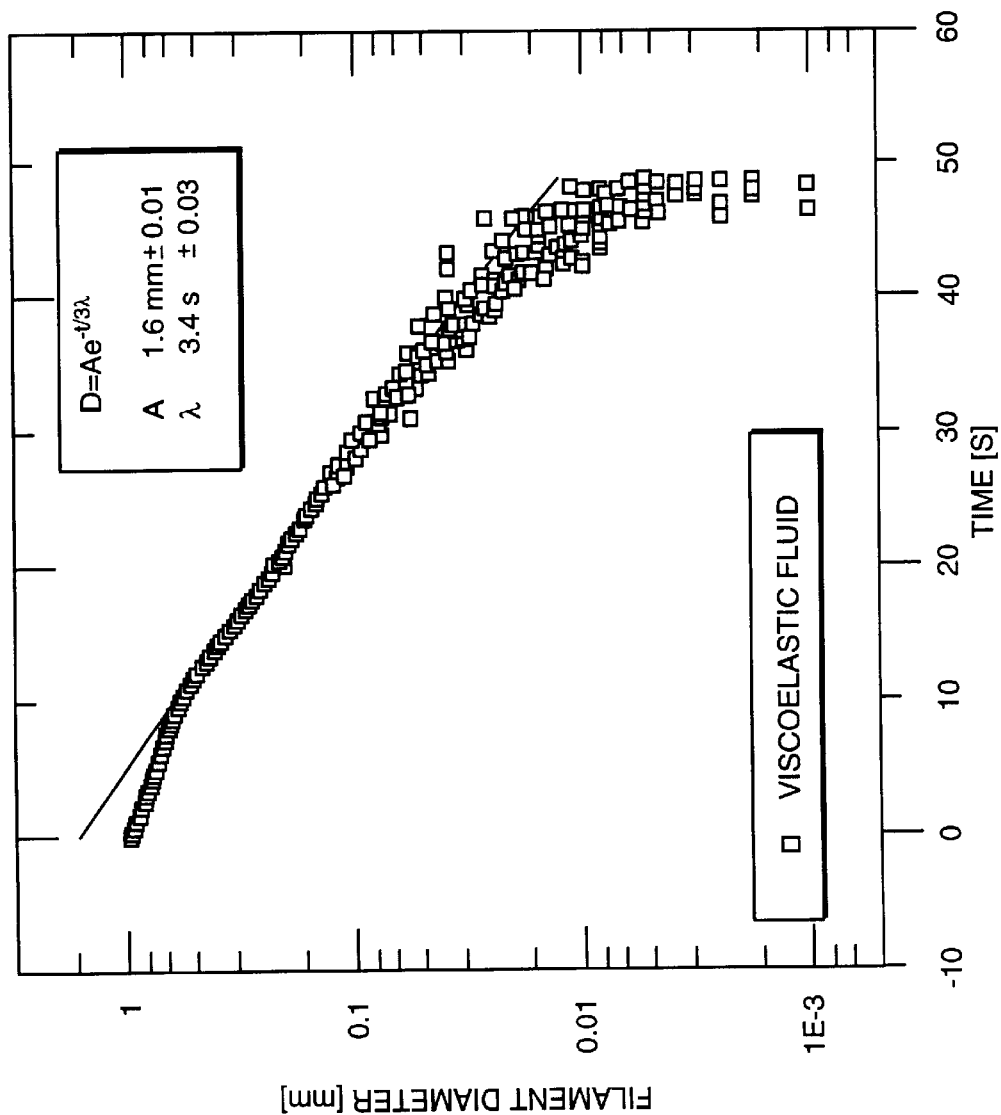
FIG. 13 shows a plot generated from data collected with an apparatus according to one embodiment of the invention.

The above discussion is applicable only for constant viscosity Newtonian fluids. In viscoelastic solutions and melts, theoretical work and subsequent numerical analysis show that following a rapid initial viscous-dominated phase, there is an intermediate time-scale in which the dynamics of the filament drainage are governed by a balance between surface tension and elasticity, rather than fluid viscosity. See, Bazilevsky et al., "Liquid Filament Microrheometer and Some of Its Applications," D. R. Oliver, Ed., *Proceedings of the Third European Rheology Conference* (Elsevier, 1990); Entov et al., *J. Non-Newtonian Fluid Mech.* 72, 31–53 (1997); Bousfield et al., *Journal of Non-Newtonian Fluid Mechanics* 21, 79–97 (1986); and Renardy, *Journal of Non-Newtonian Fluid Mechanics* 59, 267–282 (1995). In this regime, the filament radius decreases exponentially as equation (2):

$$D_{mid}(t) = D_0 \left(\frac{GD_0}{\sigma}\right)^{1/3} e^{-t/3\lambda_c} \qquad (2)$$

where $\lambda_c$ is a characteristic relaxation time governing the capillary breakup, and G is the elastic modulus of the filament. For a semi-dilute model elastic fluid, $\lambda_c$ is closely related to the longest relaxation time, $\lambda_1$ of the fluid. See, Kolte et al., *Journal of Rheology* 43, 609–626 (1999). These authors also show how the effects of a radial inhomogeneity in the stretch can account for the remaining discrepancy between $\lambda_c$ and $\lambda_1$. By choosing an appropriate aspect ratio it is possible to use measurements of the exponential decrease in radius with time to quantitatively determine: (i) the longest (Rouse/Zimm) relaxation time for ideal elastic fluids (consisting of dilute solutions of monodisperse polystyrene); and (ii) the approximate scaling of the steady-state elongational viscosity with molecular weight. See, Anna et al., *Journal of Rheology* 45(1), 115–138 (2001). For a model elastic fluid, a simple exponential fit yields the material relaxation time. An example of such a fit is shown in FIG. 13, which shows a semi-logarithmic plot of necking in a viscoelastic fluid fitted using a decaying exponential. The relaxation time of the fluid is found from the slope to be $\lambda=3.4$ s.

Complex Materials

In the two previous subsections it is clear that given the correct theoretical foundation, the instrument can extract values of material properties such as the capillary velocity, $\lambda/\eta_s$, the relaxation time, $\lambda_c$, and modulus, G, of simple test fluids. However, such idealized fluids are rarely encountered in industrial applications. In reality, commercial material formulations can often display a number of complex responses. These complexities originate from the presence of components such as volatile solvents, phase separating materials, associative materials, chemical changes (such as curing) and yield stresses. Consequently, many materials have viscometric properties that are very different in extension when compared to shear, and that also evolve with time. The capillary breakup rheometer is ideal for the study/quantification of these materials because of the short experimental times required for each. A brief list of some example materials are given below:

Absorption: Glycerol is a highly hygroscopic material that absorbs water from the atmosphere and hence shows a marked viscosity change with time.

Setting: Adhesives/wet spinning/melt spinning. Materials that set or dry are common in many fields. For example, see, FIGS. 3a and 3b.

Curing and gelation: Epoxies. Materials that are self associating or are chemically curing also change their rheological properties with time.

Generic Model—Full Force Balance

To fully encompass the complex phenomena listed above, a new generic model is required that encompasses time-varying Newtonian and non-Newtonian effects. A balance of forces on the fluid filament governs the evolution of the midpoint profile of the liquid bridge. For a slender fluid filament this force balance can be written compactly in the following form:

$$\underbrace{3\eta_s\left(-\frac{2}{D_m}\frac{dD_m}{dt}\right)}_{\text{Viscous Stress}} = 3\eta_s\dot{\varepsilon} = \underbrace{\frac{4F_2}{\pi D_m^2}}_{\text{Tensile Stress}} - \underbrace{[\tau_{zz} - \tau_{rr}]}_{\substack{\text{Elastic/Non-}\\\text{Newtonian Stress}}} - \underbrace{\frac{2\sigma}{D_m}}_{\substack{\text{Capillary}\\\text{Pressure}}} \quad (3)$$

where σ is the surface tension of the fluid, $F_z$ is the tensile force acting on the column ends, $\eta_s$ is the Newtonian viscosity of the solvent, and $[\tau_{zz}-\tau_{rr}]$ represents the non-Newtonian contribution to the total normal stress difference in the fluid. See Renardy, *Journal of Non-Newtonian Fluid Mechanics* 59, 267–282 (1995). The term $[\tau_{zz}-\tau_{rr}]$ is model-dependent and the resulting solution to the differential equation depends on how the polymeric contribution to the stress varies with the rate of deformation. Solutions to this evolution equation have been found for a number of models and are summarized in Table 1. See, Entov et al., *J. Non-Newtonian Fluid Mech.* 72, 31–53 (1997); Bazilevsky et al., A. N. Rozhkov, *Polym. Sci., Ser. A* 39, 316–324 (1997); and McKinley et al., *Journal of Rheology* 44 (2000). More complicated multi-mode models predict a spectrum of relaxation times, which is more realistic for real polymeric fluids. These models will usually capture the initial more rapid decay in radius during relaxation. This initial rapid drop is usually attributed to the relaxation of shorter time scales, after which point the longer time scales yield a more gradual radial decay and the diameter decay is dominated by the primary relaxation mode.

TABLE 1

Evolution of the Midpoint Diameter in a Fluid Thread Undergoing Capillary-Driven Breakup.

| Constitutive Model | Form of Solution | Parameters found from regression to data |
|---|---|---|
| Newtonian, $\tau = \eta_s\dot{\gamma}$ | $D_{mid}(t) = 0.142(\sigma/\eta_s)(t_c - t)$ | $t_c$, $\sigma/\eta_s$ |
| Power-Law Fluids $\tau = K\dot{\gamma}^n$ | $D_{mid}(t) = 2^{1-n}(0.142)(\sigma/K)(t_c - t)^n$ | $t_c$, $\sigma/K$, n |
| Upper Convected Maxwell $\tau + \lambda\tau_{(1)} = \eta_p\dot{\gamma}$ | $D_{mid}(t) = D_0(GD_0/\sigma)^{1/3}\exp(-t/3\lambda_c)$ | $t_c$, $\lambda_c$, $G/\sigma$ |

Time to Breakup: In each case, one of the parameters determined is the critical time to breakup, $t_c$. This parameter is not strictly a material property but depends on the properties of the fluid, the flow geometry, and the surrounding medium (e.g., the relative humidity, or partial pressure, of the solvent). However, this parameter is of utility as a possible way of quantifying concepts such as "stringiness," "stranding" and the general processability of complex materials such as foodstuffs, shampoos, and other consumer products. Although the time to breakup is related to the capillary velocity, $\sigma/\eta_s$, it also holds information about the non-Newtonian behavior (and evolution) of the material.

The Apparent Extensional Viscosity: The principal experimental results obtained from the capillary breakup rheometer are the evolution of the midpoint diameter of fluid samples with time. This evolution is driven by the capillary pressure and resisted by the extensional stresses in the fluid. Thus, the measurements also can be represented in terms of an apparent extensional viscosity, which is defined by $\bar{\eta}_{app}(\varepsilon)=[\tau_{zz}-\tau_{rr}]_{total}/\dot{\varepsilon}(t)$, while the Hencky strain is defined as $\varepsilon=\ln(D_{mid}(t)/D_1)$. By rearranging equation 3 it can be shown that the apparent extensional viscosity is given by $$\bar{\eta}_{app}(\varepsilon) = \frac{2(X-1)\sigma}{D_{mid}}\frac{1}{\left\{-\frac{2}{D_{mid}}\frac{dD_{mid}}{dt}\right\}} = \frac{(1-2X)\sigma}{\frac{dD_{mid}}{dt}} \quad (4)$$

where the instantaneous rate of stretching of the midpoint fluid element, $\dot{\varepsilon}(t)$, is given by the term in the braces, and X is obtained from a lubrication solution (X=0.7127) (See, McKinley et al., *Journal of Rheology*, 44 (2000)). If the surface tension, σ, of the test fluid is known from independent measurements, then capillary breakup rheometer data can be replotted in the form of an extensional viscosity (see, FIGS. 3a and 3b).

Software Implementation

The theoretical analysis and complete force balance discussed above provides a complete framework for analyzing capillary breakup measurements of an arbitrary test fluid in software. The following section outlines an approach to implementing this analysis, which readily may be provided in computer software. It should be understood that computer software also may be created for operating and controlling the structure of the apparatus to obtain this data.

For simple model fluids (i.e., ideally Newtonian and ideally viscoelastic), there is little problem for the extraction of rheological parameters. The theories outlined above give straightforward ways to obtain viscosity (given the surface tension) and relaxation time. In addition, the ratio of the viscosity to surface tension, which we have termed the capillary velocity, is a good index for a Newtonian fluid. It is also straightforward to obtain a breakup time, which, as pointed out previously, can yield information about the "stringiness" of the liquid. This parameter depends critically on initial conditions, and is not easily related to rheological material properties. However, if the sample preparation is performed carefully enough, this parameter could be useful as an index.

For more complex materials, a more sophisticated analysis is required which generally can be split into two steps. The first step is model independent and assumes nothing about the properties of the material. The second step uses a fluid constitutive model to extract rheological information from the fit obtained in the first step.

Model Independent Data Fit

Initially, the data are fit to a general non-linear fit that is composed of a linear term, an exponential term, and an offset term. This first step is model independent and requires no assumed knowledge about the materials, and is therefore generic:

$$D_{mid}=A-Bt+Ce^{-Dt} \quad (5)$$

It follows that:

$$\dot{\varepsilon} = -\frac{2}{D_{mid}}\frac{dD_{mid}}{dt} = \frac{2(B+CDe^{-Dt})}{A-Bt+Ce^{-Dt}} \quad (6)$$

Figure 14:
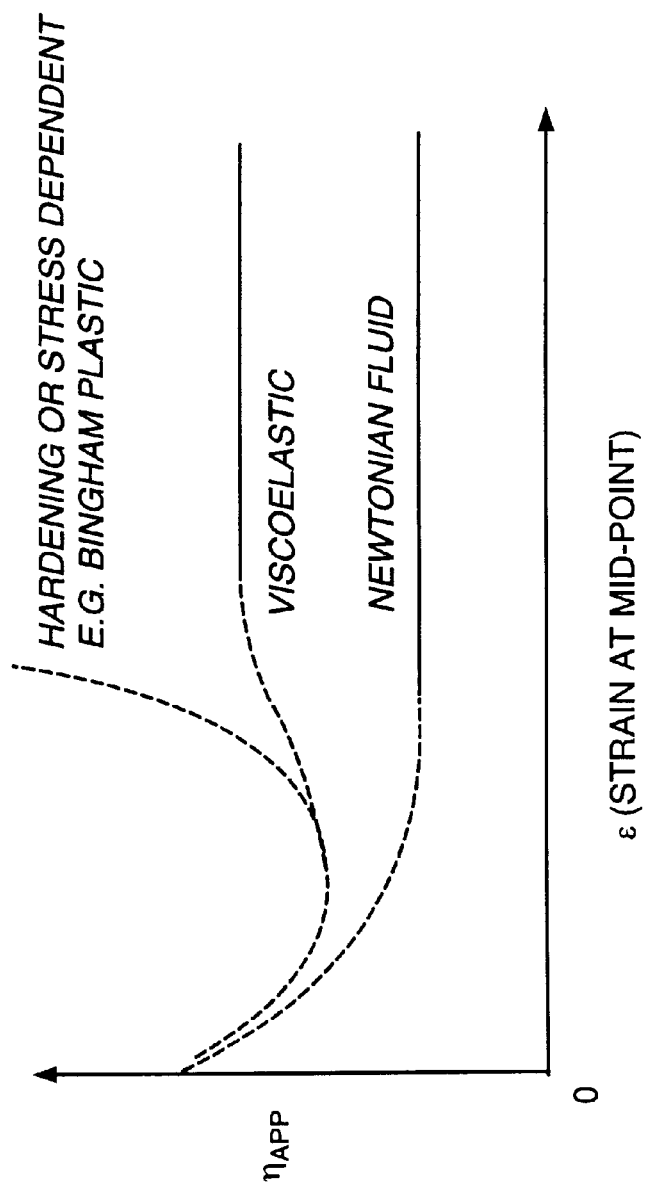
FIG. 14 shows plots depicting model independent data fit.

By invoking equation (4), the form for the strain rate in equation (6) can be used to obtain an "apparent extensional viscosity" that is composed of components resulting from the balance of the tensile, elastic, and capillary pressure forces. At this point, however, no assumptions have been made about the physical properties of the fluid. It is clear from equation (4) that the apparent viscosity relies on differentiation of the data. Hence the quality of the fit will depend on the quality of the data and/or the post processing. This formulation allows the diameter/time data to be re-plotted in the more convenient form of apparent viscosity versus strain (at the filament mid-point in the fluid). Using this concept of the apparent extensional viscosity one can obtain a visual indication of the general behavior of the fluid in an extensional flow (making the division between Newtonian, viscoelastic, and a "setting" fluid easily seen). FIG. 14, which shows the predicted behavior of apparent viscosity, and FIG. 3 show how different fluids can easily be differentiated using this approach.

Model Specific Extraction of Rheological Data

Referring back to the full force balance presented in equation (2), which makes assumptions about the fluid properties, it gives rise to a simple form for the apparent viscosity of the fluid (c.f. equation (1)) using X=0.7127 as described earlier:

$$\bar{\eta}_{APP \atop TOTAL} \equiv 3\eta_s + \bar{\eta}_{APP} = \frac{2(2X-1)\sigma}{D_m \dot{\varepsilon}} \quad (7)$$

It is a relatively simple step to use equations (4), (6) and (7) to obtain a general equation for the evolution of the filament radius. This equation provides a simple non-linear form for the evolution of the diameter over time and relates the model specific parameters to the non-linear form of equation (5), as shown in equation (8):

$$D_m(t) = \underbrace{D_1\left\{1 - \left(\frac{D_1 G}{2\sigma}\right)^{1/3}\right\}}_{A} + \underbrace{\frac{2\tau_y}{\rho g}}_{} - \underbrace{2\frac{0.0709\sigma}{\eta_s}t}_{Bt} + \underbrace{D_1\left(\frac{D_1 G}{2\sigma}\right)^{1/3} e^{-t/3\lambda_1}}_{Ce^{-Dt}} \quad (8)$$

This step assumes certain fluid properties and is therefore model dependent. However, the form of equation (8) is generally valid for Newtonian, Oldroyd-like (quasi-linear viscoelastic) and Bingham fluids. Accordingly, it encompasses, or approximates to, a large proportion of all materials likely to be met industrially. Consequently, a simple non-linear fit can be used that will allow the extraction of shear viscosity, modulus, relaxation time, and a "yield stress." In practice, this latter parameter will cover the curing and evaporation-driven setting of the filament. As before, some knowledge of the surface tension of the test material is required or the results must be given in terms of a characteristic ratio. The potential for this simple approach is clear. Table 2 outlines the parameters obtained from this model ($D_1$ is the initial diameter of the filament at t=0, $\rho$ is the density and g is gravitational acceleration).

TABLE 2

Rheological Parameters and Their Derivation from Fitted Parameters of Equation 8.

| Parameter | Ratio | Formula |
|---|---|---|
| Newtonian Viscosity | $\frac{\eta}{\sigma}$ | $\frac{\eta_s}{\sigma} = 2\frac{0.0709}{B}$ |
| Elastic Modulus | $\frac{G}{\sigma}$ | $\frac{G}{\sigma} = \frac{16C^3}{D_1^4}$ |
| Relaxation Time | $\mu$ | $\lambda = \frac{1}{3D}$ |
| Yield Stress | $\tau_y$ | $\left(\frac{2\tau_y}{\rho g}\right) = A + C - D_1$ |

Implementation

Figure 15:
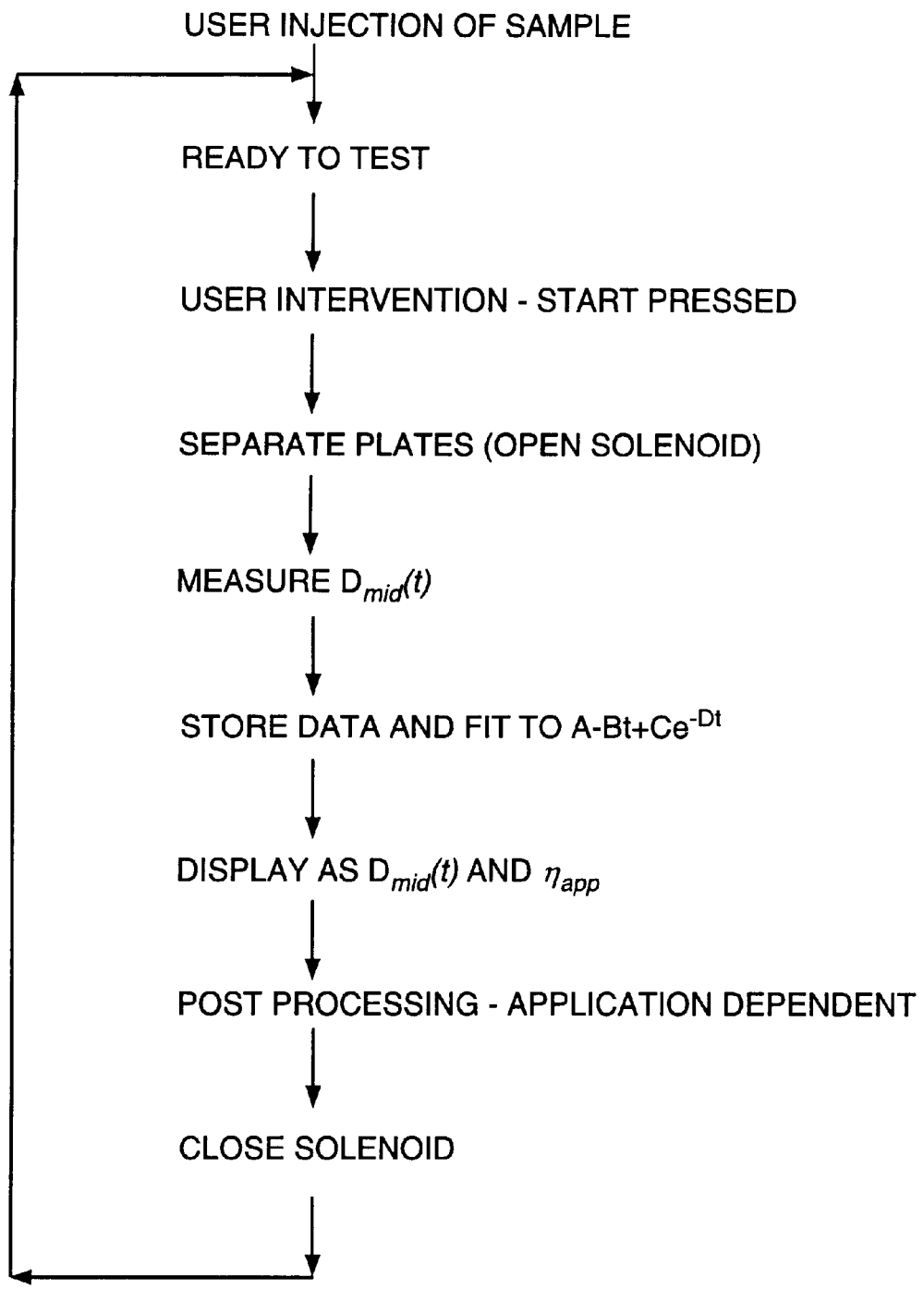
FIG. 15 is a schematic illustration of an embodiment of a method of the invention which includes software operation.

The software operates on two levels. A core experimental section obtains the time varying diameter data and determines the model independent non-linear form of equation (5). This approach allows a visual display of the effective extensional viscosity. FIG. 15 schematically outlines the operation of the software.

Entry level, or quality control (QC) version: This level has a pre-chosen model, such as the Papageorgiou or Maxwell model, for fitting to yield one parameter. This level also determines the breakup time, tc, of the filament. This data is then used in a comparison to produce an automatic "good"/"bad" decision. Different modes may be designed for different types of fluids.

Expert Level: This level uses the relationships outlined in Table 2 to obtain approximate values for the fluid parameters. Data then are fit to the equations described in Table 1 and through the quality of the fit, provides the user with a "best estimate" for the class of Theological response characterizing the fluid. This level also uses these data to plot both diameter and effective elongational viscosities and tabulate the rheological parameters. Since this section is model dependent it may require a level of expertise and knowledge from the user to interpret correctly as is true for every analytical instrument.

The above-described methods of analysis may be provided as an article of manufacture where the functionality of a method of the invention is embedded on a computer-readable program means, such as, but not limited to, a floppy disk, a hard disk, an optical disk, a magnetic tape, a PROM, an EPROM, CD-ROM, or DVD-ROM.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

Each of the patent documents disclosed hereinabove is incorporated by reference herein.

What is claimed is:

1. An apparatus for measuring an extensional rheological property of a fluid, the apparatus comprising:
    (a) opposed surfaces defining a sample site disposed therebetween and adapted for user-defined axial motion to vary the vertical dimension of the sample site;
    (b) a housing about the sample site which permits specification of ambient conditions;
    (c) a light source for directing a light beam at the sample site; and
    (d) a light detector for sensing light passing through the sample site.

2. The apparatus of claim 1 further comprising a plunger assembly for varying the vertical dimension of the sample site and for varying the rate of axial movement at a user-defined rate of at least one of the opposed surfaces.

3. The apparatus of claim 1 further comprising a data analysis unit which converts data from the light detector to an extensional rheological property of the fluid sample.

4. The apparatus of claim 2 further comprising a data analysis unit which converts data from the light detector to an extensional rheological property of the fluid sample.

5. The apparatus of claim 1 wherein the housing provides control of one or more of the temperature, the humidity, and the pressure at the sample site.

6. The apparatus of claim 1 wherein the light detector comprises a laser micrometer.

7. The apparatus of claim 6 wherein the light detector comprises a CCD camera.

8. The apparatus of claim 1 further comprising a sample loading device comprising a sleeve system allowing the measuring of a volatile fluid sample.

9. The apparatus of claim 8 wherein the sample loading device further comprises a syringe-type delivery device.

10. The apparatus of claim 9 wherein the syringe-type delivery device is manually driven, air-driven, or mechanically-activated.

11. The apparatus of claim 1 wherein at least one of the opposed surfaces is adapted for rotational motion.

12. The apparatus of claim 1 further comprising a force transducer in direct or indirect contact with at least one of the opposed surfaces.

13. The apparatus of claim 1 further comprising a heating system in thermal communication with the interior of the housing.

14. An apparatus for measuring an extensional rheological property of a fluid, the apparatus comprising
    (a) opposed surfaced defining a sample site disposed therebetween and adapted for axial motion to vary the vertical dimension of the sample site;
    (b) a plunger assembly for varying the vertical dimension of the sample site and for varying the rate of axial movement of at least one of the surfaces;
    (c) a light source for directing a light beam at the sample site; and
    (d) a light detector for sensing light passing through the sample site.

15. The apparatus of claim 14 further comprising a data analysis unit which converts data from the light detector to an extensional rheological property of the fluid sample.

16. The apparatus of claim 14 wherein the plunger assembly is connected to one of the opposed surfaces and varies the vertical dimension of the sample site by axially moving the connected surface at a user-defined rate.

17. The apparatus of claim 14 wherein the plunger assembly comprises a motor driven cam and a spring.

18. An apparatus for measuring an extensional rheological property of a fluid, the apparatus comprising
    (a) opposed surfaces defining a sample site disposed therebetween and adapted for user-defined axial motion to vary the vertical dimension of the sample site.
    (b) a light source for directing a light beam at the sample site;
    (c) a light detector for sensing light passing through the sample site; and
    (d) a data analysis unit which converts data from the light detector to an extensional rheological property of the fluid sample.

19. A method for obtaining an extensional rheological property of a fluid sample comprising the steps of:
    (a) stretching the fluid sample to form a fluid filament at a user-defined rate;
    (b) measuring a time profile of a diameter of the fluid filament; and
    (c) analyzing the time profile of the diameter of the fluid filament to obtain an extensional rheological property of the fluid sample, wherein analyzing the time profile comprises converting the time profile to a curve of viscosity versus strain.

20. The method of claim 19 further comprising repeating the step of stretching the fluid sample to form a fluid filament multiple times at various speed and measuring time profile of a diameter of the fluid filament following each stretching step.

21. The method of claim 19 further comprising isolating the fluid sample with a housing prior to the stretching and measuring steps.

22. The method of claim 19 wherein the step of measuring time profile of a diameter of the fluid filament comprises directing a beam of light to a diameter of the fluid filament and detecting light transmitted therethrough.

23. The method of claim 22 wherein the beam of light is a beam of laser light.

24. The method of claim 23 wherein detecting light transmitted through the diameter of the fluid filament comprises detecting light transmitted through the diameter of the fluid filament with a laser micrometer.

25. A portable apparatus for measuring an extensional rheological property of a fluid, the portable apparatus comprising:
    a body portion comprising:
        opposed surfaces defining a sample site disposed therebetween and adapted for axial motion to vary the vertical dimension of the sample site;
        a housing about the sample site which permits specification of ambient conditions;
        a light source for directing a light beam at the sample site; and
        a light detector for sensing light passing through the sample site; and
        a handle portion in communication with the body portion, the handle portion having a data processing device.

26. The portable apparatus of claim 25 further comprising a plunger assembly for varying the vertical dimension of the sample site and for varying the rate of axial movement at a user-defined rate of at least one of the opposed surfaces.

27. The portable apparatus of claim 25 further comprising a data analysis unit which converts data from the light detector to an extensional rheological property of the fluid sample.

28. The portable apparatus of claim 26 further comprising a data analysis unit which converts data from the light detector to an extensional rheological property of the fluid sample.

29. The portable apparatus of claim 25 wherein the housing provides control of one or more of the temperature, the humidity, and the pressure at the sample site.

30. The portable apparatus of claim 25 wherein the light detector comprises a laser micrometer.

31. The portable apparatus of claim 30 wherein the light detector comprises a charge coupled device (CCD) camera.

32. The portable apparatus of claim 25 further comprising a sample loading device comprising a sleeve system to allow the measurement of a volatile fluid sample.

33. The portable apparatus of claim 32 wherein the sample loading device further comprises a syringe-type delivery device.

34. The portable apparatus of claim 33 wherein the syringe-type delivery device is one of manually driven, air-driven, and mechanically-activated.

35. The portable apparatus of claim 25 wherein at least one of the opposed surfaces is adapted for rotational motion.

36. The portable apparatus of claim 25 further comprising a force transducer in direct or indirect contact with at least one of the opposed surfaces.

37. The portable apparatus of claim 25 further comprising a heating system in thermal communication with the interior of the housing.

38. The portable apparatus of claim 26 wherein the plunger assembly comprises a motor driven cam and a spring.

39. The portable apparatus of claim 25 further comprising a connection to interface with an external data processing device.

40. A method for analyzing an extensional rheological property of a fluid, comprising the steps of:

providing midpoint diameter measurements as a function of time of a fluid filament;

fitting the midpoint diameter measurements as a function of time to a non-linear model to obtain an approximate value of an extensional parameter;

extracting a rheological data parameter by fitting the approximate value to at least one of a plurality of appropriate models.

41. A computer readable medium having stored therein instructions for causing a central processing unit to execute the method of claim 40.

42. The method of claim 22 wherein the beam of laser light is modulated for at least one of wavelength and intensity.

43. The apparatus of claim 6 wherein at least one of resolution, response time and gain of the laser micrometer can be adjusted.

44. A method for measuring an extensional rheological property of a fluid, comprising:

measuring time varying diameter data of a fluid filament;

displaying effective extensional viscosity; and further processing the data to determine rheological parameters using a plurality of models, including a model comprising using the diameter data in a non-linear form of an equation having a linear term, an exponential term and an offset term.

45. The method of claim 44 wherein the plurality of models comprise at least one of a Newtonian model, and Maxwell model.

46. The method of claim 44 wherein the step of displaying further comprising displaying diameter and effective elongational viscosities.

* * * * *